(12) United States Patent
Chen et al.

(10) Patent No.: US 9,345,693 B2
(45) Date of Patent: *May 24, 2016

(54) MODULATORS OF ALDEHYDE DEHYDROGENASE ACTIVITY AND METHODS OF USE THEREOF

(71) Applicant: The Board of Trustees of the Leland Stanford Junior University, Palo Alto, CA (US)

(72) Inventors: Che-Hong Chen, Fremont, CA (US); Daria Mochly-Rosen, Menlo Park, CA (US); Wenjin Yang, Foster City, CA (US)

(73) Assignee: The Board of Trustees-Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,245

(22) Filed: Nov. 10, 2014

(65) Prior Publication Data

US 2015/0182511 A1  Jul. 2, 2015

Related U.S. Application Data

(60) Continuation of application No. 13/717,056, filed on Dec. 17, 2012, now Pat. No. 8,906,942, which is a division of application No. 12/553,805, filed on Sep. 3, 2009, now Pat. No. 8,354,435.

(60) Provisional application No. 61/095,227, filed on Sep. 8, 2008.

(51) Int. Cl.
*C07D 405/12* (2006.01)
*A61K 31/443* (2006.01)

(52) U.S. Cl.
CPC ............ *A61K 31/443* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 2,319,808 A | 5/1943 | Fernholz et al. |
| 4,006,239 A | 2/1977 | Mayer et al. |
| 4,861,891 A | 8/1989 | Saccomano et al. |
| 4,992,417 A | 2/1991 | Katsoyannis et al. |
| 4,992,418 A | 2/1991 | Katsoyannis et al. |
| 5,200,534 A | 4/1993 | Rao |
| 5,202,448 A | 4/1993 | Carver et al. |
| 5,229,529 A | 7/1993 | Ueno et al. |
| 5,260,323 A | 11/1993 | Baader et al. |
| 5,283,253 A | 2/1994 | Holton et al. |
| 5,294,637 A | 3/1994 | Chen et al. |
| 5,360,806 A | 11/1994 | Toki et al. |
| 5,374,605 A | 12/1994 | Hallenbach et al. |
| 5,409,907 A | 4/1995 | Blasé et al. |
| 5,415,869 A | 5/1995 | Straubinger et al. |
| 5,474,978 A | 12/1995 | Bakaysa et al. |
| 5,504,188 A | 4/1996 | Baker et al. |
| 5,514,646 A | 5/1996 | Chance et al. |
| 5,547,929 A | 8/1996 | Anderson, Jr. et al. |
| 5,650,486 A | 7/1997 | De Felippis |
| 5,693,609 A | 12/1997 | Baker et al. |
| 5,700,662 A | 12/1997 | Chance et al. |
| 5,747,642 A | 5/1998 | De Felippis |
| 5,922,675 A | 7/1999 | Baker et al. |
| 5,952,297 A | 9/1999 | De Felippis et al. |
| 6,034,054 A | 3/2000 | De Felippis et al. |
| 6,235,791 B1 | 5/2001 | Breliere et al. |
| 6,384,080 B1 | 5/2002 | Oku et al. |
| 6,762,176 B1 | 7/2004 | Chabrier de Lassauniere et al. |
| 6,780,883 B2 | 8/2004 | Booth et al. |
| 6,900,338 B1 | 5/2005 | Haj-Yehia |
| 6,939,882 B1 | 9/2005 | Cooke et al. |
| 7,179,912 B2 | 2/2007 | Halbrook |
| 7,799,782 B2 | 9/2010 | Munson |
| 8,124,389 B2 | 2/2012 | Chen et al. |
| 8,354,435 B2 | 1/2013 | Chen et al. |
| 8,389,522 B2 | 3/2013 | Mochly-Rosen et al. |
| 8,772,295 B2 * | 7/2014 | Mochly-Rosen ..... C07C 233/29 514/218 |
| 8,906,942 B2 * | 12/2014 | Chen et al. ................ 514/338 |
| 2002/0034783 A1 | 3/2002 | Meyers et al. |
| 2002/0156281 A1 | 10/2002 | Booth et al. |
| 2003/0100034 A1 | 5/2003 | Hunter |
| 2004/0234622 A1 | 11/2004 | Muto et al. |
| 2004/0242596 A1 | 12/2004 | Kim et al. |
| 2005/0171043 A1 | 8/2005 | Mochly-Rosen et al. |
| 2005/0215548 A1 | 9/2005 | Wang et al. |
| 2005/0215645 A1 | 9/2005 | Muto et al. |
| 2006/0106051 A1 | 5/2006 | Dyckman et al. |

(Continued)

FOREIGN PATENT DOCUMENTS

CN  1749415 A  3/2006
EP  1402887  3/2004

(Continued)

OTHER PUBLICATIONS

Wu, Toxicology, vol. 236, 2007, pp. 1-6.*

(Continued)

*Primary Examiner* — Zinna Northington Davis
(74) *Attorney, Agent, or Firm* — Rudy J. Ng; Paula A. Borden; Bozicevic, Field & Francis LLP

(57) ABSTRACT

The present invention provides compounds that function as modulators of aldehyde dehydrogenase activity; and pharmaceutical compositions comprising the compounds. The present invention provides therapeutic methods involving administering a subject compound, or a subject pharmaceutical composition.

19 Claims, 4 Drawing Sheets

(56) References Cited

U.S. PATENT DOCUMENTS

| | | |
|---|---|---|
| 2006/0173050 A1 | 8/2006 | Liu et al. |
| 2008/0153926 A1 | 6/2008 | Mochly-Rosen et al. |
| 2008/0200461 A1 | 8/2008 | Anderson et al. |
| 2008/0317848 A2 | 12/2008 | Gramatte |
| 2009/0082431 A1 | 3/2009 | Mochly-Rosen et al. |
| 2009/0163545 A1 | 6/2009 | Goldfarb |
| 2010/0113423 A1 | 5/2010 | Mochly-Rosen et al. |
| 2011/0105602 A2 | 5/2011 | Mochly-Rosen et al. |
| 2012/0010248 A1 | 1/2012 | Mochly-Rosen et al. |
| 2012/0101079 A1 | 4/2012 | Kuehnert et al. |
| 2013/0053362 A1 | 2/2013 | Castro et al. |
| 2013/0253010 A1 | 9/2013 | Chen et al. |
| 2013/0267501 A1 | 10/2013 | Mochly-Rosen et al. |
| 2014/0323520 A1 | 10/2014 | Chen et al. |
| 2014/0343045 A1 | 11/2014 | Mochly-Rosen |
| 2015/0105456 A1 | 4/2015 | Mochly-Rosen |
| 2015/0182506 A1 | 7/2015 | Mochly-Rosen |

FOREIGN PATENT DOCUMENTS

| | | |
|---|---|---|
| EP | 1402888 | 3/2004 |
| EP | 1438973 A1 | 7/2004 |
| EP | 1477186 A1 | 11/2004 |
| EP | 1661572 A1 | 5/2006 |
| EP | 1862552 | 1/2008 |
| EP | 2018863 | 1/2009 |
| JP | 203351 | 8/1989 |
| JP | H03184973 | 8/1991 |
| JP | 08208615 | 8/1996 |
| JP | 200526621 | 1/2005 |
| WO | WO 9710223 | 5/1997 |
| WO | 9923063 | 5/1999 |
| WO | 9932444 | 7/1999 |
| WO | 9954284 | 10/1999 |
| WO | 0112604 | 2/2001 |
| WO | 0132928 | 5/2001 |
| WO | 0222599 | 3/2002 |
| WO | 02053544 | 7/2002 |
| WO | 02064568 | 8/2002 |
| WO | 02096135 | 11/2002 |
| WO | 03064391 | 8/2003 |
| WO | 2004022523 | 3/2004 |
| WO | 2005014550 | 2/2005 |
| WO | 2005037782 | 4/2005 |
| WO | 2005037792 | 4/2005 |
| WO | 2005057213 | 6/2005 |
| WO | 2005007889 | 8/2005 |
| WO | 2005084392 | 9/2005 |
| WO | 2005011561 | 10/2005 |
| WO | 2005110422 | 11/2005 |
| WO | 2006091671 | 8/2006 |
| WO | 2007034312 | 3/2007 |
| WO | 2007075783 | 7/2007 |
| WO | 2007110237 | 10/2007 |
| WO | WO 2007136707 A2 | 11/2007 |
| WO | 2008002725 | 1/2008 |
| WO | 2008014497 | 1/2008 |
| WO | 2008021388 | 2/2008 |
| WO | 2008024497 | 2/2008 |
| WO | 2008071397 | 6/2008 |
| WO | 2008082487 | 7/2008 |
| WO | WO 2008082490 A2 | 7/2008 |
| WO | 2009146555 | 12/2009 |
| WO | 2009156484 | 12/2009 |
| WO | WO 2010028175 A1 | 3/2010 |
| WO | WO 2010062308 A1 | 6/2010 |
| WO | WO 2010137351 A1 | 12/2010 |
| WO | WO 2012082862 A2 | 6/2012 |
| WO | WO 2012106534 A2 | 8/2012 |

OTHER PUBLICATIONS

Bukhitiarova et al. "Possiblities for search for New Analagesics in the series of Arylamides of Isoniotinic and Nocotine Acids," Noi Akademii Nauk Ukraini 8: 162-164 (1998).

Bukhitiarova et al. "Structure and Anti-inflammatory Activity of Isonicotinic and Nicotine Amides," Pharmaceutical Chemistry Journal 31(11): 597-598 (1997).
Budas et al, "Activation of Aldehyde Dehydrogenase 2 (ALDH2) Confers Cardioprotection in Protein Kinase C Epsilon (PKCe) Knockout Mice," Journal of Molecular and Cellular Cardiology 48: 757-764 (2010).
Chen et al. "An Activator of Mutant and Wildtype Aldehyde Dehydrogenase Reduces Ischemic Damage to the Heart," Science 321 (5895): 1493-1495 (2008).
Chen et al. CAS: 149: 548594 (2008).
Cutshall et al. "Nicotinamide N-Oxides as CXCR2 Antagonists," Bioorganic & Medicinal Chemisrty Letters,11: 1951-1954 (2001).
Davis et al. "Requirement for Pax6 in Corneal Morphogenesis: a Role in Adhesion," Journal of Cell Science 116 (11): 2157-2167 (2003).
Deng et al. "Distinct Expression Levis and patterns of Stem Cell Marker, Aldehyde Dehydrogenase Isoform 1 (ALDH1), in Human Epithelial Cancers," PLos One 5 (4) 1-11 (2010).
Feng et al. "Isolation and Characteriaztion of Human Salivary Glands for Stem Cell Transplantation to Reduce Radiation-Induced Hyposalivation," Radiotherapy and Oncology 92:466-471 (2009).
Fernholz et al. "Stigmastadienone-22, 23-dibromide and related compounds," 1943: 40468 (1943).
Furata et al., "Efficient Synthesis of Phenanthridinone Derivatives via a Palladium-Catalyzed Coupling Process", Org. Lett. 9(2):183-186 (2007).
Gilman et al. "Organometallic Compounds in the Kolbe and Reimer-Tiemann Reactions," J.of Organic Chemisrty 1946: 2074 (1945).
Grigg et al., "Synthesis of Cyclopropanes by Intramolecular Attack of N-Nucleophiles on the Central Carbon of ($\pi$-Allyl)palladium Complexes,"Eur. J. Org. Chem. 4:707-712. (2001).
Hess et al. "Functional Characterization of Highly Purified Human Hematopoietic Repopulating Cells Isolated According to Aldehyde Dehydrogenase Activity," Blood 104(6): 1648-1655 (2004).
Himel et al., "Fluorescent analogs of insecticides and synergists. Synthesis and reactions of active-site-directed fluorescent probes," J. Arg. Food Chem 19(6): 1175-1180 (1971).
Huisgen et al., CAS: 46: 45365 (1952).
Johnson et al. "Metabolism, Excretion, and Pharmacokinetics of 3-{[4-Tert-Butylbenzy)-(Pyridine-3-sulfonyl)-Amino]-Methyl-Phenoxy)-Acetic Acid, An Ep2recepto-Selective Prostaglandin E2 Agonist, In Male and Female Sprague-Dawley Rats," Drug Metabolism and Disposition 33(8): 1191-1201 (2005).
Katritzky et al. "N-Oxides and Related Compounds. Part X. The Hydrogenation pd some Polyridine 1-oxides," J. Chem. Soc.: 1-18 (1958).
Konoplitskaya et al., "Influence of Cyclopropylethyl-Containing Amines and Amides of the Isoenzyme Forms of Rat Liver Aldehyde Dehydrogenase," 28(1): 7-10. (1994).
Larson et al., "Disruption of the Coenzyme Binding Site and Dimer Interface Revealed in the Crystal Structure of Mitochondrial Aldehde Dehydrogenase Asian Variant," The J. of Biological Chem 280 (34): 30550-30556 (2005).
Li et al., "Mitochondrial Aldehyde Dehydrongenase-2(ALDH2) Glu554Lys Polymorphism Contributes to the Variation in Efficacy of Sublingual Nitroglycerin," The J. of Clinical Investigation 116 (2): 506-511 (2006).
Lombaert et al. "Rescue of Salivary Gland Function after Stem Cell Transplantation in Irradiated Glands," PLos One 3(4) 1-13 (2008).
Moussa et al. CAS: 146: 337551 (2007).
Nicoll-Griffith, "Stereoelectronic Model to Explain the Resolution of Enantiomeric Ibuprofen Amides on the Pirkle Chiral Stationary Phase," J. of Chromatography 402: 179-187 (1987).
Nicoll-Griffith's CAS: 107 141210 (1987).
Palacios, "Diuretic Action of New Sulfonmide Compounds," Arch. Inst. Farmacol. Exptl. 16(1): 1-18 (1964).
Paruszewski et al. "Anticonvulsant Activty of Benzylamides of Some Amino Acids and Heterocyclic Acids," Protein and Peptide and Peptide Letters 10(5): 475-482 (2003).
Perez-Miller et al. "Alda-1 is an Agonist and Chemical Chaperone for the common Human Aldehyde Dehydrogenase 2 Variant," Nat Struct Mol Biol. 17(2) 159-164 (2010).

(56) References Cited

OTHER PUBLICATIONS

Registry (STN) [online], Apr. 2, 2004 (searched date: Apr. 25, 2013), CAS Registry No. 670271-74-6.
Registry (STN) [online], Apr. 24, 2001 (searched date: Apr. 25, 2013), CAS Registry No. 332129-81-4.
Registry (STN) [online], Aug. 1, 2001 (searched date Apr. 25, 2013), CAS Registry No. 349615-88-9.
Registry (STN) [online], Jan. 2, 2001 (searched date: Apr. 25, 2013), CAS Registry No. 312526-08-2.
Registry (STN) [online], Jul. 25, 2006 (searched date: Apr. 25, 2013), CAS Registry No. 895680-72-5.
Registry (STN) [online], Jul. 25, 2006 (searched date: Apr. 25, 2013), CAS Registry No. 895680-64-5.
Registry (STN) [online], Jul. 26, 2001 (searched date: Apr. 25, 2013), CAS Registry No. 348604-08-0.
Registry (STN) [online], Jul. 29, 2001 (searched date: Apr. 25, 2013), CAS Regisrty No. 349438-38-6.
Registry (STN) [online], Jun. 7, 2004 (searched date: Apr. 25, 2013), CAS Registry No. 690210-80-1.
Registry (STN) [online], May 14, 2003 (searched date: Apr. 25, 2013), CAS Registry No. 514816-37-6.
Registry (STN) [online], Nov. 5, 2004 (searched date: Apr. 25, 2013), CAS Registry No. 775317-15-2.
Sato et al. "2-hydroxymethylnicotinic Acid Lactone, 2-Hydroxymethylpyridine-3-acetic Acid Lactone, and Some of their Derivatives," Chem. Pharm. Bull. 8(5) 427-435 (1960).
Satoh et al., "Comparison of the inhibitory action of synthetic capsaicin analogues with various NADH-ubiquinone oxidoreductases," Biochimica et Biophysica Acta 1273(1):21-30 (1996).
Seto et al, "Design and Synthesis of Novel 9-substituted-7-aryl-3,4,5,6-tetrahydro-2H-pyrido [4,3-b]- and [2,3-b]- and [2,3,-b]-1,5-oxazocin-6-ones as NK1 Antagonists," Bioorganic & Medicinal Chemistry Letters 15: 1479-1484 (2005).
STN: 11/16 RN 7500-45-0 (1984).
Tracy et al. "Product class 4: N-Arylalkanamides, ynamides, enamides, dienamides and allenamides," Science of Synthesis 2006:359121 (2005).
Weintraub et al., CAS: 143405804 (2005).
Zhang et al., "Automation of Fluorous Solid-Phase Extraction for Parallel Synthesis," J. Comb. Chem. 8(6):890-896 (1994).
Messiha and Hughes "Liver Alcohol and Aldehyde Dehydrogenase Inhibition and Potentiation by histamine Agonists and Antagonists," Clinical and Experimental Pharmacology and physiology 6(3) 281-292 (1979).
Registry (STN) [online], Jun. 5, 2001(searched date:Dec. 19, 2013), CAS Registry No. 339335-56-7.
Borgna et al., "Preparation and Study of the Phytotoxic Activity of N-Aralkyl Substituted Amides," 11 Farmaco; Edizione Scientifica 32 (11): 813-826 (1977).
Patani et al., "Bioisosterism A Rational Approach in Drug Design," Chem Rev. 96: 3146-3176 (1996).
Stella and NTI-ADDAE, "Prodrug Strategies to Overcome Poor Water Solubility," Department of Pharm Chem 59:677-694 (2007).
Williams et al., "Drug Design and Relationship of Functional Groups to Pharmacologic Activity," Foye's Principles of Medicinal Chemistry 5: 50 and 59-61 (2002).
Chaturvedi, A. K. et. al., "Effects of choline acetyltransferase inhibitors on the growth and differentiation of mouse neuroblastoma cells in culture", Research Communications in Chemical Pathology and Pharmacology, 37(3), 491-494 (1982).
Chung, W. K. et el. "Synthesis and antitumor activities of potential antineoplastic agents. IV. Synthesis and antitumor activities of N-substituted-p-arsanilic acid", Yakhak Hoechi, 1971, 15(1), 16-23 & Caplus Accession No. 1974:115993
Dimmock et al. "Evaluation of some mannich bases derived from substituted acetophenones against p-388 Lymphocycitc leukemia and on respiration in isolated rat liver mitochondria," J. Pharmaceutical Sciences 72(8) 887-894 (1983).
Gul, H. I. et al. "Evaluation of the cytotoxicity of some mono-Mannich bases and their corresponding azine derivatives against androgen-independent prostate cancer cells", Arzneim.-Forsch./Drug Res., 56(12), 850-855 (2006).
Huang, et al., "Antineoplastic activities of 2,3,4-chloro-substituted β-alkylaminopropiophenone derivatives in CF1 mice and in murine and human tumor cells" (Experimental Report), Anti-Cancer Drugs, 7, 613-620 (1996).
Leone et al., The effects of Melatonin and Melatonin Analogues on the P388, DLD-1 and MCF-7 Tumour Cell Lines, NATO ASI series A: Life Sciences 241-242 (1991).
Malyugina et al., "Antitumor action of some derivatives of adrenalones," Pharmaceutical Chemistry Journal 13(7): 56-58 (1979).
Registry (STN) [online], Dec. 21, 1990 (searched date:), CAS Registry No. 131139-67-8.
Werner, W. et al. "Structure-effect interactions in Mannich bases with and without nitrogen-mustard groups and some reduction products derived from β-aminoketones on the basis of a cancerostatic-3-step test with transplantation tumors", Pharmazie, 32(6): 341-347 & Caplus Accession No. 1977:545546 (1977).
Werner, W. et al. "Relations between the chemical structure of Mannich bases with and without nitrogen mustard groups and their cytostatic activisty against Ehrlich ascites carcinoma in mice," Arzneimittel-Forschung 20(2): 246-249 (1970).
Chen et al. "Interactive effects of lifetime alcohol consumption and alcohol and aldehyde dehydrogenase polymorphisms on esophageal cancer risks," Int J Cancer; 119(12):2827-2831 (2003).
Hashibe et al. "Evidence for an Important Role of Alcohol- and Aldehyde-Metabolizing Genes in Cancers of the Upper Aerodigestive Tract," Cancer Epidemiol Biomarkers Prev.; 15(4):696-703 (2006).
Hashimoto et al. "ALDH2 1510 G/A (Glu487Lys) polymorphism interaction with age in head and neck squamous cell carcinoma," Tumour Biol; 27(6):334-338 (2006).
Yokoyama et al. "Genetic Polymorphisms of Alcohol and Aldehyde Dehydrogenases and Risk for Esophageal and Head and Neck Cancers," Alcohol; 35(3):175-185 (2005).
U.S. Appl. No. 14/774,071, filed Sep. 9, 2015, Yang et al.
Weber "Decker-Oxidation 2-Substituierter N-Alkylpyridiniumverbindungen, 5 Mitt. Die Decker-Oxidation Von Homarin", Archiv Der Pharmazie, Wiley Verlag, Weinheim, 309(7): 664-669, XP001026698, ISSN: 0365-6233, DOI: 10.1002/ARDP. 19763090810 (1976).
White et al. "Specific sequestering agents for the actinides. 16. Synthesis and initial biological testing of polydentate oxohydroxypyridinecarboxylate ligands", Journal of Medical Chemistry, 31(1): 11-18 (1988).

\* cited by examiner

```
  1 mlraaarfgp rlgrrllsaa atqavpapnq qpevfcnqif innewhdavs rktfptvnps
 61 tgevicqvae gdkedvdkav kaaraafqlg spwrrmdash rgrllnrlad lierdrtyla
121 aletldngkp yvisylvdld mvlkclryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnlk rvtlelggks pniimsdadm
301 dwaveqahfa lffnqgqccc agsrtfvqed iydefversv araksrvvgn pfdskteqgp
361 qvdetqfkki lgyintgkqe gakllcgggi aadrgyfiqp tvfgdvqdgm tiakeeifgp
421 vmqilkfkti eevvgranns tyglaaavft kdldkanyls qalqagtvwv ncydvfgaqs
481 pfggykmsgs grelgeyglq aytevktvtv kvpqkns (SEQ ID NO:1)
```

FIG. 1A

```
  1 mlraaarfgp rlgrrllsaa atqavpapnq qpevfcnqif innewhdavs rktfptvnps
 61 tgevicqvae gdkedvdkav kaaraafqlg spwrrmdash rgrllnrlad lierdrtyla
121 aletldngkp yvisylvdld mvlkclryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnlk rvtlelggks pniimsdadm
301 dwaveqahfa lffnqgqccc agsrtfvqed iydefversv araksrvvgn pfdskteqgp
361 qvdetqfkki lgyintgkqe gakllcgggi aadrgyfiqp tvfgdvqdgm tiakeeifgp
421 vmqilkfkti eevvgranns tyglaaavft kdldkanyls qalqagtvwv ncydvfgaqs
481 pfggykmsgs grelgeyglq aytkvktvtv kvpqkns (SEQ ID NO:2)
```

FIG. 1B

ALDH1
*Homo sapiens*
AAC51652

```
  1 msssgtpdlp vlltdlkiqy tkifinnewh dsvsgkkfpv fnpateeelc qveegdkedv
 61 dkavkaarqa fqigspwrtm dasergrlly kladlierdr lllatmesmn ggklysnayl
121 sdlagciktl rycagwadki qgrtipidgn fftytrhepi gvcgqiipwn fplvmliwki
181 gpalscqntv vvkpaeqtpl talhvaslik eagfppgvvn ivpgygptag aaisshmdid
241 kvaftgstev gklikeaagk snlkrvtlel ggkspcivla dadldnavef ahhgvfyhqg
301 qcciaasrif veesiydefv rrsverakky ilgnpltpgv tqppqidkeq ydkildlies
361 gkkegaklec gggpwgnkgy fvqptvfsnv tdemriakee ifgpvqqimk fksldddvikr
421 anntfyglsa gvftkdidka itissalqag tvwvncygvv saqcpfggfk msgngrelge
481 ygfheytevk tvtvkisqkn s (SEQ ID NO:3)
```

FIG. 2A

ALDH1
*Homo sapiens*
NM_000689 = nucleotide sequence
NP_000680 = amino acid sequence

```
  1 msssgtpdlp vlltdlkiqy tkifinnewh dsvsgkkfpv fnpateeelc qveegdkedv
 61 dkavkaarqa fqigspwrtm dasergrlly kladlierdr lllatmesmn ggklysnayl
121 ndlagciktl rycagwadki qgrtipidgn fftytrhepi gvcgqiipwn fplvmliwki
181 gpalscqntv vvkpaeqtpl talhvaslik eagfppgvvn ivpgygptag aaisshmdid
241 kvaftgstev gklikeaagk snlkrvtlel ggkspcivla dadldnavef ahhgvfyhqg
301 qcciaasrif veesiydefv rrsverakky ilgnpltpgv tqppqidkeq ydkildlies
361 gkkegaklec gggpwgnkgy fvqptvfsnv tdemriakee ifgpvqqimk fksldddvikr
421 anntfyglsa gvftkdidka itissalqag tvwvncygvv saqcpfggfk msgngrelge
481 ygfheytevk tvtvkisqkn s (SEQ ID NO:4)
```

FIG. 2B

ALDH3
*Homo sapiens*
AAB26658

```
  1  mskiseavkr apaafssgrt rplqfriqql ealqrliqeq eqelvgalaa dlhknewnay
 61  yeevvyvlee ieymiqklpe waadepvekt pqtqqdelyi hseplgvvlv igtwnypfnl
121  tiqpmvgaia agnsvvlkps elsenmasll atiipqyldk dlypvinggv pettellker
181  fdhilytgst gvgkiimtaa akhltpvtle lggkspcyvd kncdldvacr riawgkfmns
241  gqtcvapdyi lcdpsiqnqi veklkkslke fygedakksr dygriisarh fqrvmglieg
301  qkvayggtgd aatryiapti ltdvdpqspv mqeeifgpvl pivcvrslee aiqfinqrek
361  plalymfssn dkvikkmiae tssggvaand vivhitlhsl pfggvgnsgm gsyhgkksfe
421  tfshrrsclv rplmndeglk vryppspakm tqh (SEQ ID NO:5)
```

FIG. 3

MODULATORS OF ALDEHYDE DEHYDROGENASE ACTIVITY AND METHODS OF USE THEREOF

CROSS-REFERENCE

This application is a continuation of U.S. application Ser. No. 13/717,056, filed Dec. 17, 2012, now U.S. Pat. No. 8,906, 942 which is a divisional of U.S. application Ser. No. 12/553, 805 filed Sep. 3, 2009, now U.S. Pat. No. 8,354,435, which claims the benefit of U.S. Provisional Patent Application No. 61/095,227, filed Sep. 8, 2008, the disclosures of each of which applications are incorporated herein by reference in their entirety.

GOVERNMENT SUPPORT

This invention was made with Government support under contract AA011147 awarded by the National Institutes of Health. The Government has certain rights in the invention.

BACKGROUND

Aldehyde dehydrogenases (ALDH) constitute a family of enzymes that play a critical role in detoxification of various cytotoxic xenogenic and biogenic aldehydes. There are at least 19 members/isozymes of the ALDH family, where the various isozymes may exhibit different substrate specificity and/or cellular location relative to other members of the family.

Cytotoxic aldehydes derive from a variety of sources. For example, environmental (external) sources of aldehydes include those that result from ethanol consumption, consumption of food sources, or from ingestion of hazardous materials such as vinyl chloride, pesticides, herbicides, etc. Aldehydes that may be cytotoxic can also be produced biologically, e.g., as a result of oxidative stress such as occurs in ischemia, irradiation, or metabolism or bioconversion of cellular precursors such as neurotransmitters and drugs. Accumulation of cytotoxic levels of aldehydes, and/or defects in the ALDH enzyme, has been implicated in a variety of diseases and conditions, or in increased risk of disease development. The range of implicated diseases includes neurodegenerative diseases, aging, cancer, myocardial infarction, stroke, dermatitis, diabetes, and liver diseases.

Mitochondrial aldehyde dehydrogenase-2 (ALDH2) is encoded in the nuclear genome and is transported into mitochondria. ALDH2 is a tetrameric protein composed of four identical subunits, each consisting of 500 amino acid residues. This tetramer can be regarded as a dimer of dimers. The interface between monomers that form a dimer is different and more extensive than the interface between the two dimers that form the tetramer. Each subunit is composed of three main domains: the catalytic domain, the coenzyme or $NAD^+$-binding domain, and the oligomerization domain.

There is a need in the art for modulators of aldehyde dehydrogenase enzymatic activity.

LITERATURE

Larson et al. (2005) *J. Biol. Chem.* 280:30550; Li et al. (2006) *J. Clin. Invest.* 116:506; US Patent Publication No. 2005/0171043; WO 2005/057213; WO 2008/112164.

SUMMARY OF THE INVENTION

The present invention provides compounds that function as modulators of aldehyde dehydrogenase activity; and pharmaceutical compositions comprising the compounds. The present invention provides therapeutic methods involving administering a subject compound, or a subject pharmaceutical composition.

BRIEF DESCRIPTION OF THE DRAWINGS

FIG. 1A and FIG. 1B provide the amino acid sequence of human ALDH2 (SEQ ID NO:1) and the amino acid sequence of an E487K variant of human ALDH2, respectively.

FIGS. 2A and 2B provide exemplary ALDH1 amino acid sequences.

FIG. 3 provides an exemplary ALDH3 amino acid sequence.

DEFINITIONS

Figure 4:
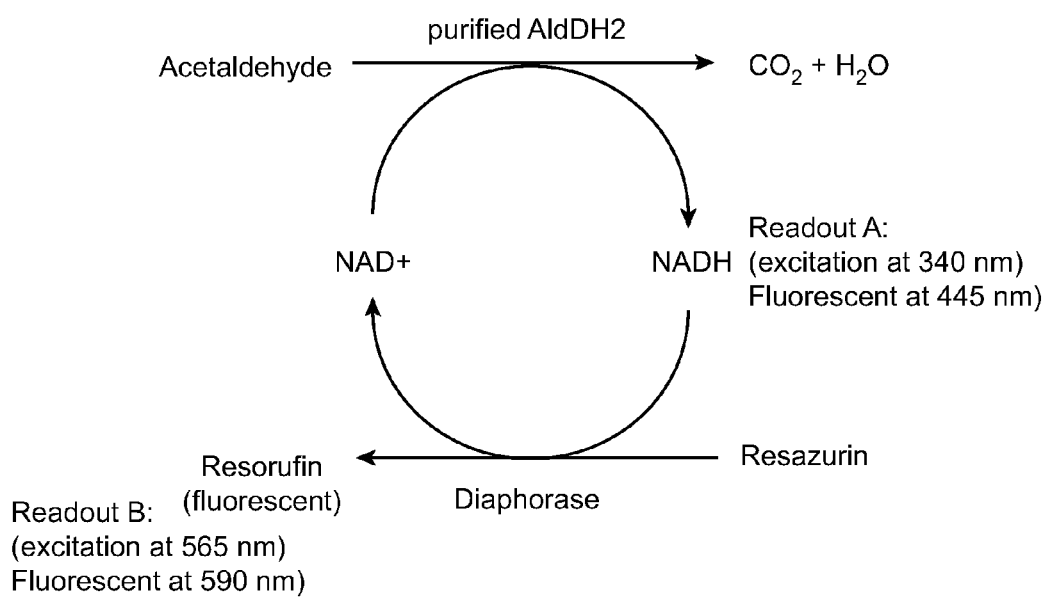
FIG. 4 schematically depicts a fluorescent aldehyde dehydrogenase enzymatic assay.

As used herein, the term "aldehyde dehydrogenase" or "ALDH" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent or an $NADP^+$-dependent reaction. For example, ALDH oxidizes aldehydes derived from the breakdown of compounds, e.g., toxic compounds that are ingested, that are absorbed, that are inhaled, or that are produced during normal metabolism. An example of a biogenic aldehyde is acetaldehyde produced as a product of alcohol dehydrogenase activity on ingested ethanol.

As used herein, the term "aldehyde dehydrogenase" or "ALDH" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent or an $NADP^+$-dependent reaction. For example, ALDH oxidizes aldehydes derived from the breakdown of compounds, e.g., toxic compounds that are ingested, that are absorbed, that are inhaled, that are produced as a result of oxidative stress, or that are produced during normal metabolism, e.g., conversion of retinaldehyde to retinoic acid. An example of a biogenic aldehyde is acetaldehyde produced as a product of alcohol dehydrogenase activity on ingested ethanol. An aldehyde dehydrogenase can also exhibit esterase activity and/or reductase activity.

The term "ALDH" encompasses ALDH found in the cytosol, in the mitochondria, microsome, or other cellular compartment. The term "ALDH" encompasses ALDH found primarily in one or a few tissues, e.g., cornea, saliva, liver, etc., or in stem cells and embryos. The term "ALDH" encompasses any of the known ALDH isozymes, including ALDH1, ALDH2, ALDH3, ALDH4, ALDH5, etc.

As used herein, the term "mitochondrial aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent reaction. For example, ALDH2 oxidizes aldehydes derived from the breakdown of compounds, e.g., toxic compounds that are ingested, that are absorbed, that are inhaled, or that are produced during normal metabolism. Mitochondrial ALDH2 is naturally found in mitochondria.

The term "ALDH2" encompasses ALDH2 from various species. Amino acid sequences of ALDH2 from various species are publicly available. For example, a human ALDH2 amino acid sequence is found under GenBank Accession Nos.

AAH02967 and NP_000681; a mouse ALDH2 amino acid sequence is found under GenBank Accession No. NP_033786; and a rat ALDH2 amino acid sequence is found under GenBank Accession No. NP_115792. The term "ALDH2" encompasses an aldehyde dehydrogenase that exhibits substrate specificity, e.g., that preferentially oxidizes aliphatic aldehydes. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1 (FIG. 1A) or SEQ ID NO:2 (FIG. 1B).

The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of human ALDH2, as depicted in FIG. 1B (amino acid 504 of SEQ ID NO:2), or at a position corresponding to amino acid 487 of human ALDH2. This mutation is referred to as the "E487K mutation"; the "E487K variant"; or as the "Glu504Lys polymorphism". See, e.g., Larson et al. (2005) *J. Biol. Chem.* 280:30550; and Li et al. (2006) *J. Clin. Invest.* 116:506. An ALDH2 variant retains at least about 1% of the enzymatic activity of a corresponding wild-type ALDH2 enzyme. For example, the E487K variant retains at least about 1% of the activity of an enzyme comprising the amino acid sequence depicted in FIG. 1A (SEQ ID NO:1). "ALDH2" includes an enzyme that converts acetaldehyde into acetic acid, e.g., where the acetaldehyde is formed in vivo by the action of alcohol dehydrogenase on ingested ethanol.

As used herein, "ALDH1" refers to a cytosolic aldehyde dehydrogenase that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent reaction.

The term "ALDH1" encompasses ALDH1 from various species. Amino acid sequences of ALDH1 from various species are publicly available. See, e.g., GenBank Accession Nos. AAC51652 (*Homo sapiens* ALDH1); NP_000680 (*Homo sapiens* ALDH1); AAH61526 (*Rattus norvegicus* ALDH1); AAI05194 (*Bos taurus* ALDH1); and NP_036051 (*Mus musculus* ALDH1). The term "ALDH1" as used herein also encompasses fragments, fusion proteins, and variants (e.g., variants having one or more amino acid substitutions, addition, deletions, and/or insertions) that retain ALDH1 enzymatic activity. The term "ALDH1" encompasses an aldehyde dehydrogenase that oxidizes aromatic aldehydes, including those of the naphthaldehyde, phenanthrenealdehyde, and coumarinaldehyde series, as well as complex polyaromatic aldehydes. The term "ALDH1" encompasses a cytosolic aldehyde dehydrogenase. ALDH1 does not accept the coenzyme $NADP^+$, but instead uses the coenzyme $NAD^+$.

The term "ALDH1" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in SEQ ID NO:3 or SEQ ID NO:4 (depicted in FIGS. 2A and 2B, respectively).

The term "ALDH3" encompasses ALDH3 from various species. Amino acid sequences of ALDH3 from various species are publicly available. See, e.g., GenBank Accession Nos. AAB26658 (*Homo sapiens* ALDH3), NP_000683 (*Homo sapiens* ALDH3), P30838 (*Homo sapiens* ALDH3), NP_001106196 (*Mus musculus* ALDH3), and AAH70924 (*Rattus norvegicus* ALDH3). The term "ALDH3" as used herein also encompasses fragments, fusion proteins, and variants (e.g., variants having one or more amino acid substitutions, addition, deletions, and/or insertions) that retain ALDH3 enzymatic activity. The term "ALDH3" encompasses an aldehyde dehydrogenase that exhibits specificity toward aromatic aldehydes, e.g., oxidizing aromatic aldehydes of the 2-naphthaldehyde series, but inactive toward 1-naphthaldehydes and higher polyaromatic aldehydes. The term "ALDH3" encompasses an aldehyde dehydrogenase that can use both $NAD^+$ and $NADP^+$ as co-substrate. The term "ALDH3" encompasses aldehyde dehydrogenase found naturally in saliva and in the cornea.

The term "ALDH3" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in SEQ ID NO:5 (as depicted in FIG. 3).

The term "ALDH5" (also referred to as "succinic semialdehyde dehydrogenase") encompasses an $NAD^+$-dependent enzyme that oxidizes succinic semialdehyde to succinate. ALDH5 is involved in the catabolism of 4-aminobutyric acid (GABA). Naturally-occurring ALDH5 can be found in the mitochondria of eukaryotic cells. The term "ALDH5" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in GenBank Accession No. AAH34321.

The term "isolated compound" means a compound which has been substantially separated from, or enriched relative to, other compounds with which it occurs in nature. Isolated compounds are at least about 80%, at least about 90% pure, at least about 95% pure, at least about 98% pure, or at least about 99% pure, by weight. The present invention is meant to comprehend diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The terms "subject," "individual," and "patient" are used interchangeably herein to a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human mammals having commercial importance (e.g., livestock and domesticated animals) are of particular interest.

"Mammal" refers to a member or members of any mammalian species, and includes, by way of example, canines; felines; equines; bovines; ovines; rodentia, etc. and primates, e.g., humans. Non-human animal models, particularly mammals, e.g. a non-human primate, a murine (e.g., a mouse, a rat), lagomorpha, etc. may be used for experimental investigations.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to one or more of the generic formulas shown below in vivo when such prodrug is administered to a mammalian subject. Prodrugs of a compound of one or more of the generic formulas shown below are prepared by modifying functional groups present in the compound of the generic formula in such a way that the modifications may be cleaved in vivo to release the parent compound. Prodrugs include compounds of one or more of the generic formulas shown below wherein a hydroxy, amino, or sulfhydryl group in one or more of the generic formulas shown below is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N- dimethylaminocarbonyl) of hydroxy functional groups in compounds of one or more of the generic formulas shown below, and the like.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

A subject compound may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an ALDH agonist" includes a plurality of such agonists and reference to "the pharmaceutical composition" includes reference to one or more pharmaceutical compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides compounds that function as modulators of aldehyde dehydrogenase (ALDH) enzymatic activity, as well as compositions and formulations comprising the compounds. The present invention provides therapeutic methods involving administering a subject compound, or a subject pharmaceutical composition.

Agonists of ALDH (e.g., ALDH1, ALDH2, ALDH3, ALDH4, ALDH5, etc.) are useful for treating a variety of disorders, including, e.g., conditions involving ischemic stress, chronic free-radical associated diseases, acute free-radical associated diseases, insensitivity to nitroglycerin (e.g., in angina and heart failure), hypertension, diabetes, and osteoporosis. Agonists of ALDH are also useful for reducing the level in an individual of a compound such as ethanol, methanol, ethylene glycol monomethyl ether, polyvinyl chloride, xenogenic aldehydes, and biogenic aldehydes. Agonists of ALDH are also useful for reducing the level in an individual of a compound that, when ingested, absorbed, or inhaled, gives rise to an aldehyde substrate for ALDH. The present invention provides therapeutic methods involving administering a subject compound, or a subject pharmaceutical composition.

In some embodiments, individuals to be treated are humans. In some embodiments, a human to be treated according to a subject method is one that has two "wild-type" ALDH2 alleles, e.g., the ALDH2 encoded by the two wild-type ALDH2 alleles has a glutamic acid at position 487, as depicted in FIG. 1A. In other embodiments, a human to be treated according to a subject method is one that has one or two "ALDH2*2" alleles, e.g., the ALDH2 encoded by one or both ALDH2 alleles comprises a lysine as amino acid position 487, as depicted in FIG. 1B. The E487K polymorphism is a semidominant polymorphism, and results in an ALDH2 tetramer that has significantly lower enzymatic activity than "wild-type" ALDH2. Thus, individuals who are heterozygous or homozygous for the ALDH2*2 allele have much lower in vivo ALDH2 activity levels than individuals who are homozygous for the "wild-type" ALDH2 allele. Individuals who are heterozygous or homozygous for the ALDH2*2 allele are expected to benefit from treatment with a subject ALDH2 agonist, because the level of ALDH2 activity in such individuals is particularly low, and any increase of ALDH2 activity levels would be expected to provide a therapeutic effect. Any increase in ALDH2 activity would be beneficial in treating conditions such as ischemic disorders, in increasing the responsiveness of such individuals to nitroglycerin, etc., as discussed in more detail below.

Modulators of Aldehyde Dehydrogenase

The present invention provides compounds that function as modulators of aldehyde dehydrogenase (ALDH) activity; and pharmaceutical compositions comprising the compounds. The present invention provides compounds that function as modulators of mitochondrial aldehyde dehydrogenase-2 (ALDH2) activity; and pharmaceutical compositions comprising the compounds.

In some embodiments, a subject ALDH agonist increases activity of a "wild-type ALDH2 enzyme. In other embodiments, a subject ALDH agonist increases activity of a variant ALDH2 enzyme that comprises an E→K substitution at amino acid 487 of the mature enzyme. In some embodiments, a human to be treated according to a subject method is one that has two "wild-type" ALDH2 alleles, e.g., the ALDH2 encoded by the two wild-type ALDH2 alleles has a glutamic acid at position 487 of the mature protein (amino acid 504 of the protein including the leader peptide), as depicted in FIG. 1A. In other embodiments, a human to be treated according to a subject method is one that has one or two "ALDH2*2" alleles, e.g., the ALDH2 encoded by one or both ALDH2 alleles comprises a lysine as amino acid position 487 of the mature protein (amino acid 504 of the protein including the leader peptide), as depicted in FIG. 1B. The E487K polymorphism is a semidominant polymorphism, and results in an ALDH2 tetramer that has significantly lower enzymatic activity than "wild-type" ALDH2. Thus, individuals who are heterozygous or homozygous for the ALDH2*2 allele have much lower in vivo ALDH2 activity levels than individuals who are homozygous for the "wild-type" ALDH2 allele. Individuals who are heterozygous or homozygous for the ALDH2*2 allele are expected to benefit from treatment with a subject ALDH2 agonist, because the level of ALDH2 activity in such individuals is particularly low, and any increase of ALDH2 activity levels would be expected to provide a therapeutic effect. Any increase in ALDH2 activity would be beneficial in treating conditions such as ischemic disorders, in increasing the responsiveness of such individuals to nitroglycerin, etc., as discussed in more detail below.

In some embodiments, a subject ALDH agonist selectively modulates (e.g., increases) an enzymatic activity of a particular ALDH isozyme. For example, in some embodiments, a subject ALDH agonist selectively increases an enzymatic activity of ALDH1. For example, in some embodiments, a subject ALDH agonist increases an enzymatic activity of ALDH1, but does not substantially increase the same enzymatic activity of an ALDH isozyme other than ALDH1, e.g., the ALDH agonist increases an enzymatic activity of an ALDH isozyme other than ALDH1, if at all, by no more than about 15%, e.g., by less than 15%, less than 10%, less than 5%, or less than 1%.

In some embodiments, a subject ALDH agonist selectively modulates (e.g., increases) an enzymatic activity of a particular ALDH isozyme. For example, in some embodiments, a subject ALDH agonist selectively increases an enzymatic activity of ALDH2. For example, in some embodiments, a subject ALDH agonist increases an enzymatic activity of ALDH2, but does not substantially increase the same enzymatic activity of an ALDH isozyme other than ALDH2, e.g., the ALDH agonist increases an enzymatic activity of an ALDH isozyme other than ALDH2, if at all, by no more than about 15%, e.g., by less than 15%, less than 10%, less than 5%, or less than 1%.

In some embodiments, a subject ALDH agonist selectively modulates (e.g., increases) an enzymatic activity of a particular ALDH isozyme. For example, in some embodiments, a subject ALDH agonist selectively increases an enzymatic activity of ALDH3. For example, in some embodiments, a subject ALDH agonist increases an enzymatic activity of ALDH3, but does not substantially increase the same enzymatic activity of an ALDH isozyme other than ALDH3, e.g., the ALDH agonist increases an enzymatic activity of an ALDH isozyme other than ALDH3, if at all, by no more than about 15%, e.g., by less than 15%, less than 10%, less than 5%, or less than 1%.

In some embodiments, a subject ALDH agonist increases enzymatic activity of both ALDH2 and ALDH1. In some embodiments, a subject ALDH agonist increases enzymatic activity of both ALDH2 and ALDH1, but does not substantially increase enzymatic activity of an ALDH isozyme other than ALDH2 and ALDH1. In some embodiments, a subject ALDH agonist increases enzymatic activity of both ALDH1 and ALDH2, where the ALDH2 comprises a lysine at amino acid 487 of the mature protein (amino acid 504 of the protein including the leader peptide) as depicted in FIG. 1B.

A subject ALDH agonist will in some embodiments increases an enzymatic activity of an ALDH for a particular substrate or class of substrates. For example, in some embodiments, a subject ALDH agonist increases an enzymatic activity of an ALDH3 enzyme for complex polyaromatic aldehydes such as phenanthrenealdehyde. As another example, a subject ALDH agonist increases an enzymatic activity of an ALDH1 enzyme for a substrate such as phenylacetaldehyde. As another example, a subject ALDH agonist increases an enzymatic activity of an ALDH1 enzyme for a naphthaldehyde derivative of the phenanthrene series. As another example, a subject ALDH agonist increases an enzymatic activity of an ALDH3 enzyme for a long-chain aliphatic aldehyde (e.g., 6-methyoxy-2-naphthaldehyde; 2-naphthaldehyde; 6-dimethylamino-2-naphthaldehyde; etc.). As another example, a subject ALDH agonist increases an enzymatic activity of an ALDH2 enzyme (either wild-type or E487K variant, or both) for acetaldehyde.

In some embodiments, a compound that modulates ALDH activity modulates a dehydrogenase activity of ALDH, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, a compound that modulates ALDH activity modulates an esterase activity of ALDH. In other embodiments, a compound that modulates ALDH activity modulates a reductase activity of ALDH. For example, ALDH can convert nitroglycerin to nitric oxide (NO) via its reductase activity.

As noted above, in some embodiments, a compound that modulates ALDH activity modulates a dehydrogenase activity of ALDH, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid.

A variety of compounds can give rise to aldehyde substrates for ALDH (e.g., ALDH2). Non-limiting examples of compounds that can give rise to aldehyde substrates for ALDH include ethanol; a variety of insecticides; industrial toxins such as vinyl chlorides (e.g., polyvinyl chloride); and pyruvate. For example, a compound is ingested, absorbed (e.g., through the skin), or inhaled, by a mammal and is subsequently converted in the mammal into an aldehyde substrate for ALDH.

Biogenic aldehydes include aldehydes that are produced by a mammal, e.g., are produced metabolically by a mammal. Non-limiting examples of biogenic aldehydes include ω-6 polyunsaturated fatty acids, such as malondialdehyde (MDA); 3,4-dihydroxypheylacetaldehyde (DOPAL); 3,4-dihydroxyphenylglycolaldehye (DOPEGAL); hexanal; acrolein; glyoxal; crotonaldehyde; trans-2-nonenal; 4-oxo-2-nonenal; and 4-hydroxy-2-nonenal (HNE) (see e.g., Ellis, Pharmacology & Therapeutics (2007) 115:13, Picklo and Montine (2007) J Alzheimers Dis. 12:185); 3-aminopropanal (3-AP), a product of polyamine oxidase; and aldehyde products of tyrosine, serine and threonine (see Wood et al, Brain Res (2006) 1095; 190); and retinaldehdye (see e.g. Chen et al, Molecular Pharmacology (1994) 46:88). A further example of a biogenic aldehyde is acetaldehyde formed as a product of alcohol dehydrogenase activity on ingested ethanol.

Xenogenic aldehydes include aldehydes ingested, absorbed, or inhaled by a mammal from source outside the mammal. Xenogenic aldehydes include, e.g., formaldehyde and glutaraldehyde (e.g., McGregor et al., Crit Rev Toxicol (2006) 36:821 and Pandey et al Hum Exp. Toxicol. (2000) 19:360); chloroacetaldehyde (see e.g., Richardson et al., Mutat. Research (2007) 636:178); and reactive aldehydes present in cigarette smoke (see Simth et al., Inhal. Toxicol. (2006) 18:667).

Non-limiting examples of compounds that are substrates for ALDH include 3,4-dihydroxypheylacetaldehyde (DOPAL); 3,4-dihydroxyphenylglycolaldehye (DOPEGAL); acrolein; formaldehyde; acetaldehyde; propionaldehyde; n-butyraldehyde; capronaldehyde; heptaldehyde; pentaldehyde; octylaldehyde; decylaldehyd; retinaldehyde; 3-hydroxybenzaldehyde; 2,5-dihydroxybenzaldehyde; phenylacetaldehyde; 3-phenylpropionaldehyde (see, e.g., Want et al. (2002) *Drug Metabolism and Disposition* 30:69); cinnamoyl and hydrocinnamoyl aldehydes and their derivative aldehydes (e.g. p-nitrocinnamaldehyde, p-(dimethylamino) cinnamaldehyde, hydrocinnamaldehyde, phenylpropionaldehyde); benzaldehyde and its derivative aldehydes (e.g. 2,4-dinitro-benzaldehyde, o-nitro-benzaldehyde, p-nitrobenzaldehyde, p-methyl-benzaldehyde, m-methyl-benzaldehyde, p-methoxy-benzaldehyde, p-(dimethylamino)-benzaldehyde, m-methoxy-benzaldehyde, m-hydroxy-benzaldehyde, 3,4-dimethoxy-benzaldehyde, o-methoxy-benzaldehyde); naphthaldehyde and its derivative aldehydes (e.g. 5-bromo-1-naphthaldehyde, 5-nitro-1-naphthaldehyde, 6-[O—(CH$_2$)$_5$—COOH]-2-naphthaldehyde, 6-(dimethylamino)-2-naphthaldehyde); coumarin-4-carboxaldehyde and its derivative aldehydes (e.g. 7-acetoxy-coumarin-4-carboxaldehyde, 7-(dimethylamino)-coumarin-4-carboxaldehyde, 7-methoxy-coumarin-4-carboxaldehyde, 6,7-dimethoxy-coumarin-4-carboxaldehyde); quinoline, quinolinonecarboxaldehyde, and their derivative aldehydes (e.g. quinoline-3-carboxaldehyde, 7-(dimethylamino)-2-quinolinone-4-carboxaldehyde, quinoline-4-carboxaldehyde, 6-methoxy-2-quinolinone-4-carboxaldehyde); phenanthrene-9-carboxaldehyde; indole-3-aldehyde, indole-3-actaldehyde; 5-methoxyindole-3-carboxaldehyde; 3-pyridinecarboxaldehyde; fluorene-2-carboxaldehyde (see, e.g., Klyosov, (1996) *Biochemistry* 35:4457); 4-hydroxynonenal; malondialdehyde; 3,4-dihydroxyphenylacetaldehyde; and 5-hydroxylindole-3-acetaldehyde. See, also, e.g., Williams et al. (2005) *Anal. Chem.* 77:3383; Marchitti et al. (2007) *Pharmacol. Rev.* 59:125; and Hoffman and Maser (2007) *Drug Metab. Rev.* 39:87.

ALDH Agonists

The present invention provides ALDH agonists (also referred to as "activators"); and pharmaceutical compositions comprising ALDH agonists. In other embodiments, a subject ALDH agonist is selective for ALDH2. In some embodiments, a subject ALDH agonist is also an agonist for one or more ALDH isozymes in addition to ALDH2. In some embodiments, a subject ALDH agonist is also an agonist for ALDH2 and ALDH1. In other embodiments, a subject ALDH agonist is also an agonist for ALDH2 and ALDH3. In some embodiments, a one or more of the compounds discussed in WO 2008/112164 is specifically excluded.

A subject ALDH agonist is useful for treating a variety of disorders, including, e.g., conditions involving ischemic stress, chronic free-radical associated diseases, acute free-radical associated diseases, insensitivity to nitroglycerin (e.g., in angina and heart failure), hypertension, diabetes, seizures, cancer, acute myocardial infarction, stroke, skin damage, dermatitis, atherosclerosis, Alzheimer's Disease, Parkinson's Disease, and osteoporosis. A subject ALDH agonist is also useful in the detoxification of alcohol abuse, methanol poisoning, ethylene glycol monomethyl ether poisoning, and poisoning due to other xenogenic or biogenic aldehyde compounds.

In some embodiments, a subject ALDH agonist exhibits enhanced solubility in a physiological solution. A "physiological solution" includes various bodily fluids (e.g., blood, serum, plasma, cerebrospinal fluid, urine, etc.); buffers such as a Tris buffer, N-(2-Hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-Morpholino)propanesulfonic acid (MOPS), N-tris[hydroxymethyl]methyl-3-aminopropanesulfonic acid (TAPS); a physiological saline solution (e.g., 0.9% NaCl); and the like. In some embodiments, a subject ALDH agonist has a solubility of from about 10 mM to about 100 mM or more (e.g., from about 10 mM to about 25 mM, from about 25 mM 50 mM, from about 50 mM to about 75 mM, from about 75 mM to about 100 mM, or greater than 100 mM) in 0.9% NaCl at a temperature in the range of from about 22° C. to about 40° C. (e.g., from about 22° C. to about 25° C., from about 25° C. to about 30° C., from about 30° C. to about 35° C., or from about 35° C. to about 40° C.).

In some embodiments, a subject ALDH agonist exhibits enhanced solubility in a physiological solution, compared to a compound described in, e.g., WO 2008/112164. For example, in some embodiments, a subject ALDH agonist exhibits at least about 20%, at least about 25%, at least about 30%, at least about 35%, at least about 40%, at least about 50%, at least about 75%, at least about 2-fold, at least about 2.5-fold, at least about 3-fold, at least about 5-fold, at least about 7-fold, or at least about 10-fold, or greater than 10-fold, increased solubility in a liquid (e.g., a biologically compatible liquid; a pharmaceutically acceptable liquid), compared to the solubility of another ALDH agonist (e.g., a compound described in WO 2008/112164) in the same liquid. As an example, in some embodiments, a subject ALDH agonist has a solubility of from about 10 mg/ml to about 1 g/ml in water at 22° C., e.g., in some embodiments, a subject ALDH agonist has a solubility of from about 10 mg/ml to about 25 mg/ml, from about 25 mg/ml to about 50 mg/ml, from about 50 mg/ml to about 100 mg/ml, from about 100 mg/ml to about 200 mg/ml, from about 200 mg/ml to about 300 mg/ml, from about 300 mg/ml to about 400 mg/ml, from about 400 mg/ml to about 500 mg/ml, from about 500 mg/ml to about 600 mg/ml, from about 600 mg/ml to about 700 mg/ml, from about 700 mg/ml to about 800 mg/ml, or from about 800 mg/ml to about 1 g/ml in water at 22° C. In some embodiments, a subject ALDH agonist has a solubility of from about 10 mg/ml to about 25 mg/ml, from about 25 mg/ml to about 50 mg/ml, from about 50 mg/ml to about 100 mg/ml, from about 100 mg/ml to about 200 mg/ml, from about 200 mg/ml to about 300 mg/ml, from about 300 mg/ml to about 400 mg/ml, from about 400 mg/ml to about 500 mg/ml, from about 500 mg/ml to about 600 mg/ml, from about 600 mg/ml to about 700 mg/ml, from about 700 mg/ml to about 800 mg/ml, or from about 800 mg/ml to about 1 g/ml in an aqueous solution at 22° C. solubility of from about 10 mg/ml to about 25 mg/ml, from about 25 mg/ml to about 50 mg/ml, from about 50 mg/ml to about 100 mg/ml, from about 100 mg/ml to about 200 mg/ml, from about 200 mg/ml to about 300 mg/ml, from about 300 mg/ml to about 400 mg/ml, from about 400 mg/ml to about 500 mg/ml, from about 500 mg/ml to about 600 mg/ml, from about 600 mg/ml to about 700 mg/ml, from about 700 mg/ml to about 800 mg/ml, or from about 800 mg/ml to about 1 g/ml in an organic solvent at 22° C. In some embodiments, a subject ALDH agonist has a solubility of from about 1 mg/ml to about 10 mg/ml in water at 22° C., in an aqueous solution at 22° C., or in an organic solvent at 22° C.

In some embodiments, a subject ALDH agonist exhibits enhanced bioavailability, e.g., increased oral bioavailability. For example, the bioavailability can be greater than 60%, greater than 65%, greater than 70%, greater than 75%, greater than 80%, greater than 85%, greater than 90%, greater than 95%, greater than 98%, or greater than 99%.

A subject ALDH agonist increases an enzymatic activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH polypeptide in the absence of the agonist.

In some embodiments, a subject ALDH agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH polypeptide in the absence of the agonist.

In some embodiments, a subject ALDH agonist increases the esterase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH polypeptide in the absence of the agonist.

In some embodiments, a subject ALDH agonist increases the reductase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH polypeptide in the absence of the agonist.

In some embodiments, a subject ALDH agonist increases an enzymatic activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, a subject ALDH agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, a subject ALDH agonist increases an esterase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, a subject ALDH agonist increases a reductase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, a subject ALDH agonist increases an enzymatic activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, a subject ALDH agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, a subject ALDH agonist increases an esterase activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, a subject ALDH agonist increases a reductase activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, a subject ALDH agonist increases an enzymatic activity (e.g., an aldehyde dehydrogenase activity, a reductase activity, or an esterase activity) of an ALDH1 polypeptide comprising an amino acid sequence set forth in SEQ ID NO:3 or 4 (depicted in FIGS. 2A and 2B, respectively), by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH1 polypeptide in the absence of the agonist.

In some embodiments, a subject ALDH agonist increases an enzymatic activity (e.g., an aldehyde dehydrogenase activity, a reductase activity, or an esterase activity) of an ALDH3 polypeptide comprising an amino acid sequence set forth in SEQ ID NO:5 (depicted in FIG. 3), by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH3 polypeptide in the absence of the agonist.

In some embodiments, a subject ALDH agonist is specific for (e.g., selective for) ALDH2, e.g., a subject ALDH2 agonist increases an enzymatic activity of an ALDH2 enzyme, but does not substantially increase the same enzymatic activity of cytosolic aldehyde dehydrogenase-1 (ALDH1), e.g., a subject ALDH2 agonist increases an enzymatic activity of an ALDH1 enzyme, if at all, by less than about 15%, less than about 10%, less than about 5%, less than about 2%, or less than about 1%, when used at a concentration that increases the same enzymatic activity of an ALDH2 enzyme by at least about 5% or more. In some embodiments, a subject ALDH2 agonist does not substantially increase the enzymatic activity of alcohol dehydrogenase (ADH), e.g., a subject ALDH2 agonist increases the enzymatic activity of an ADH, if at all, by less than about 5%, less than about 2%, or less than about 1%, when used at a concentration that increases the enzymatic activity of an ALDH2 enzyme by at least about 5% or more.

For example, in some embodiments, a subject ALDH agonist is specific for (e.g., selective for) ALDH2, e.g., a subject ALDH2 agonist increases dehydrogenase activity of an ALDH2 enzyme, but does not substantially increase the dehydrogenase activity of cytosolic aldehyde dehydrogenase-1 (ALDH1), e.g., a subject ALDH2 agonist increases dehydrogenase activity of an ALDH1 enzyme, if at all, by less than about 15%, less than about 10%, less than about 5%, less than about 2%, or less than about 1%, when used at a concentration that increases dehydrogenase activity of an ALDH2 enzyme by at least about 5% or more. In some embodiments, a subject ALDH2 agonist does not substantially increase dehydrogenase activity of alcohol dehydrogenase (ADH), e.g., a subject ALDH2 agonist increases the dehydrogenase activity of an ADH, if at all, by less than about 5%, less than about 2%, or less than about 1%, when used at a concentration that increases the dehydrogenase activity of an ALDH2 enzyme by at least about 5% or more.

In some embodiments, a subject ALDH agonist is specific for (e.g., selective for) ALDH1, e.g., a subject ALDH agonist increases an enzymatic activity of an ALDH1 enzyme, but does not substantially increase the same enzymatic activity of any other ALDH isozyme, e.g., a subject ALDH agonist increases an enzymatic activity of an ALDH isozyme other than ALDH1, if at all, by less than about 15%, less than about 10%, less than about 5%, less than about 2%, or less than about 1%, when used at a concentration that increases the same enzymatic activity of an ALDH1 enzyme by at least about 15% or more.

In some embodiments, a subject ALDH agonist is specific for (e.g., selective for) ALDH3, e.g., a subject ALDH agonist increases an enzymatic activity of an ALDH3 enzyme, but does not substantially increase the same enzymatic activity of any other ALDH isozyme, e.g., a subject ALDH agonist increases an enzymatic activity of an ALDH isozyme other than ALDH3, if at all, by less than about 15%, less than about 10%, less than about 5%, less than about 2%, or less than about 1%, when used at a concentration that increases the same enzymatic activity of an ALDH3 enzyme by at least about 15% or more.

In some embodiments, a subject ALDH agonist increases an enzymatic activity of both ALDH1 and ALDH2, but does not does not substantially increase the same enzymatic activity of any other ALDH isozyme, e.g., a subject ALDH agonist increases an enzymatic activity of an ALDH isozyme other than ALDH1 and ALDH2, if at all, by less than about 15%, less than about 10%, less than about 5%, less than about 2%, or less than about 1%, when used at a concentration that increases the same enzymatic activity of an ALDH1 and ALDH2 enzyme by at least about 15% or more.

In some embodiments, a subject ALDH agonist has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

For example, in some embodiments, a subject ALDH agonist has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM, for a dehydrogenase activity of mitochondrial ALDH2.

In some embodiments, a subject ALDH2 agonist has an $EC_{50}$ for an ALDH2 polypeptide comprising an amino acid sequence set forth in SEQ ID NO:1 (depicted in FIG. 1A), or as set forth in amino acids 18-517 of SEQ ID NO:1, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

For example, in some embodiments, a subject ALDH2 agonist has an $EC_{50}$ for dehydrogenase activity of an ALDH2 polypeptide comprising an amino acid sequence set forth in SEQ ID NO:1 (depicted in FIG. 1A), or as set forth in amino acids 18-517 of SEQ ID NO:1, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH2 agonist has an $EC_{50}$ for an ALDH2 polypeptide comprising an amino acid sequence set forth in SEQ ID NO:2 (depicted in FIG. 1B), or as set forth in amino acids 18-517 of SEQ ID NO:2, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH2 agonist has an $EC_{50}$ for dehydrogenase activity of an ALDH2 polypeptide comprising an amino acid sequence set forth in SEQ ID NO:2 (depicted in FIG. 1B), or as set forth in amino acids 18-517 of SEQ ID NO:2, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH agonist has an $EC_{50}$ for an enzymatic activity (e.g., an aldehyde dehydrogenase activity, an esterase activity, a reductase activity) of an ALDH1 polypeptide of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH agonist has an $EC_{50}$ for an enzymatic activity (e.g., an aldehyde dehydrogenase activity, an esterase activity, a reductase activity) of an ALDH3 polypeptide of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH2 agonist is a compound of generic Formula I, as shown below:

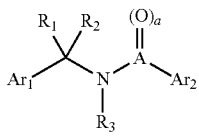

Formula I where each of $R_1$, $R_2$, and $R_3$ is independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S and where a=1 when A=C; and where a=2 when A=S; and where $Ar_1$ and $Ar_2$ are independently selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

For example, in some embodiments, $Ar_1$ of Formula I are independently:

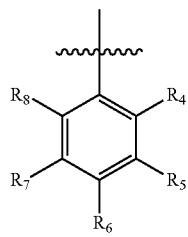

where $R_4$-$R_8$ are each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group. In other embodiments, $Ar_1$ of Formula I are independently a substituted or unsubstituted heterocyclic group, e.g., a substituted or unsubstituted pyridine, a thiazole, an imidazole, a thiophene, a quinoline, an isoquinoline, or a furan group.

In exemplary embodiments of Formula I, $Ar_2$ of Formula I is independently a substituted pyridine oxide. For example, in exemplary embodiments of Formula I, $Ar_2$ of Formula I is independently a substituted pyridine oxide selected from the formulas,

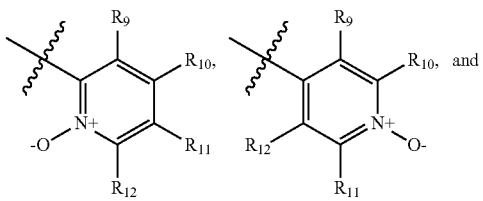

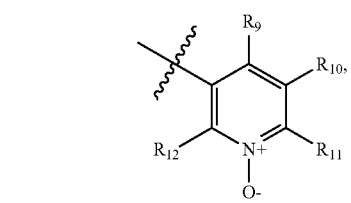

where $R_9$ to $R_{12}$ is each independently selected from H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group.

In some embodiments, a subject ALDH agonist is a compound of generic Formula II, as shown below:

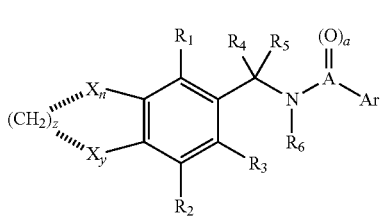

Formula II where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond; where z is the integer 0, 1, or 2;

where A is C or S, and where a=1 when A=C; and where a=2 when A=S;

where Ar is an unsubstituted or substituted aryl group, a substituted heteroaryl group, or an unsubstituted heteroaryl group; and where $R_1$ to $R_6$ is each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

or a pro-drug, a pharmaceutically acceptable salt, an analog, or a derivative thereof.

In exemplary embodiments of Formula II, Ar is independently a substituted pyridine oxide. For example, in exemplary embodiments of Formula II, Ar is independently a substituted pyridine oxide selected from a formula shown below,

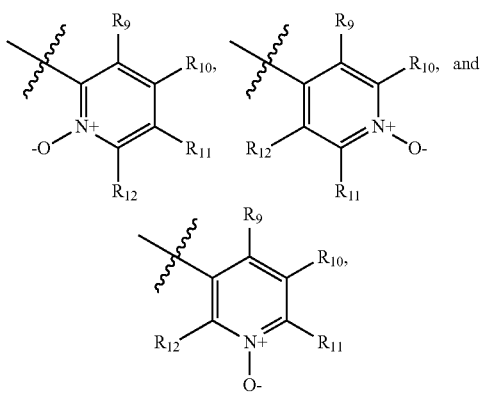

where $R_9$ to $R_{12}$ is each independently selected from a group including, but not limited to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group.

In some embodiments, a subject ALDH agonist is a compound of generic formula Ia, as shown below:

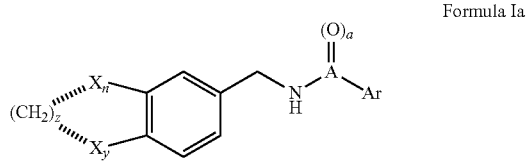

Formula Ia where $X_n$ and $X_y$ are each independently H, C, N, O, or a halogen (e.g., F, Br, Cl, or I);

where . . . (dotted line) is an optional bond;

where z is the integer 0, 1, or 2, with the provisos that: 1) z=0 when X=halogen and is not a bond; and 2) when z=0, X=O, . . . is not a bond, and one or more oxygen atoms (X) are present, oxygen is attached to a methyl group;

where n is the integer 0 or 1;

where y is the integer 0 or 1;

where A=C or S, and where a=1 when A=C; and where a=2 when A=S;

where Ar is independently a substituted pyridine oxide selected the formula from below,

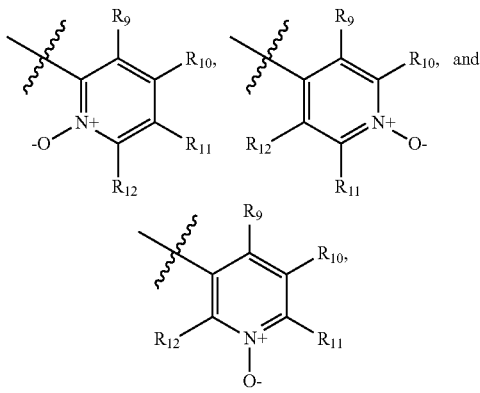

where $R_9$ to $R_{12}$ is each independently selected from a group including, but not limit to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group;

or a pro-drug, a pharmaceutically acceptable salt, an analog, or a derivative thereof.

In some embodiments, a subject ALDH agonist has the structure of Formula a, as shown below.

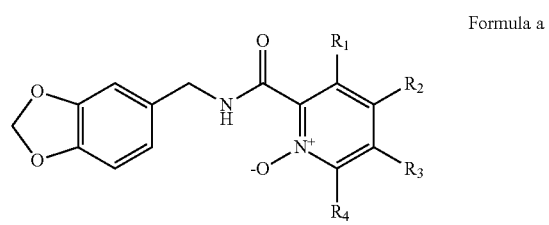

Formula a where $R_1$ to $R_4$ is each independently selected from, but not limited to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester or an amide group;

or a pro-drug, a pharmaceutically acceptable salt, an analog, or a derivative thereof.

The following are exemplary, non-limiting compounds within Formula a.

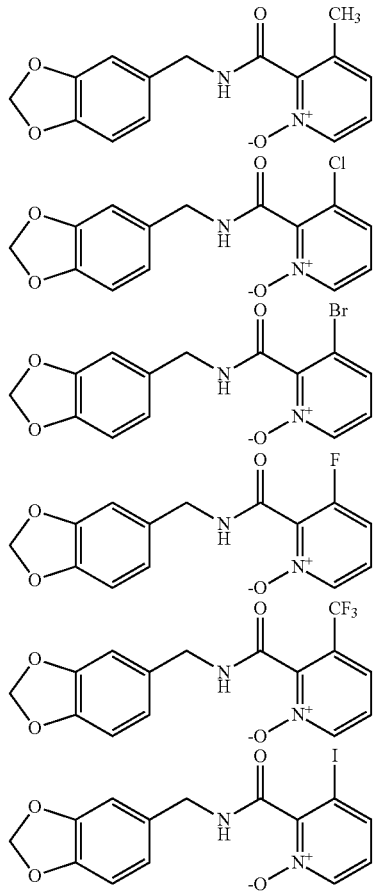

-continued

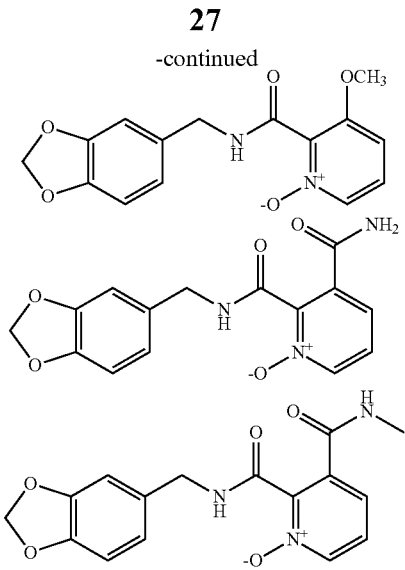

In some embodiments, a subject ALDH agonist has the structure of Formula b, as shown below.

Formula b

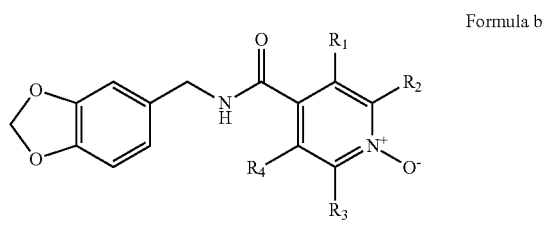

where $R_1$ to $R_4$ is each independently selected from, but not limit to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group;

or a pro-drug, a pharmaceutically acceptable salt, an analog, or a derivative thereof.

The following are exemplary, non-limiting compounds of Formula b:

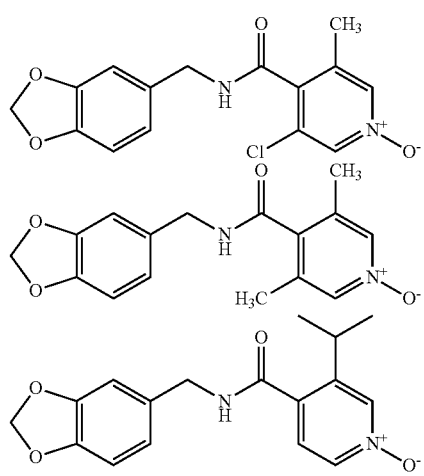

-continued

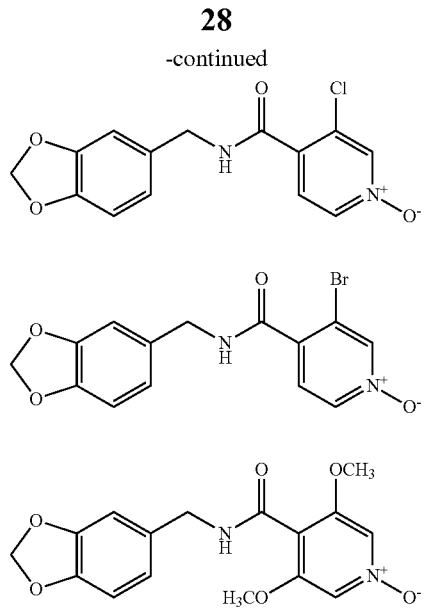

In some embodiments, a subject ALDH agonist has the structure of Formula c, as shown below.

Formula c

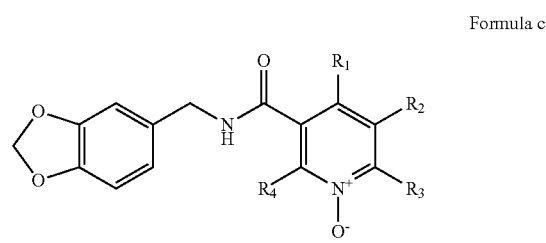

where $R_1$ to $R_4$ is each independently selected from such group, but not limit to, H; a halo (e.g., bromo, fluoro, chloro, iodo); an aliphatic group; an alkyl group; a substituted alkyl group; an alkenyl group; an alkynyl group; a substituted or unsubstituted cyclic group; an ether; a substituted or unsubstituted amine; an ester; and an amide group;

or a pro-drug, a pharmaceutically acceptable salt, an analog, or a derivative thereof.

The following are exemplary, non-limiting compounds of Formula c:

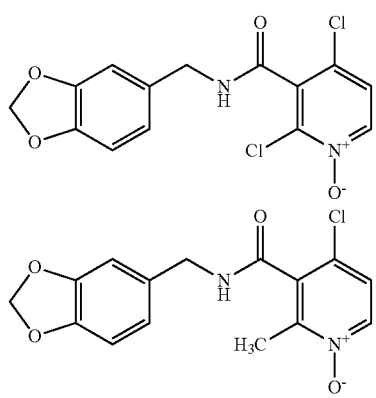

-continued

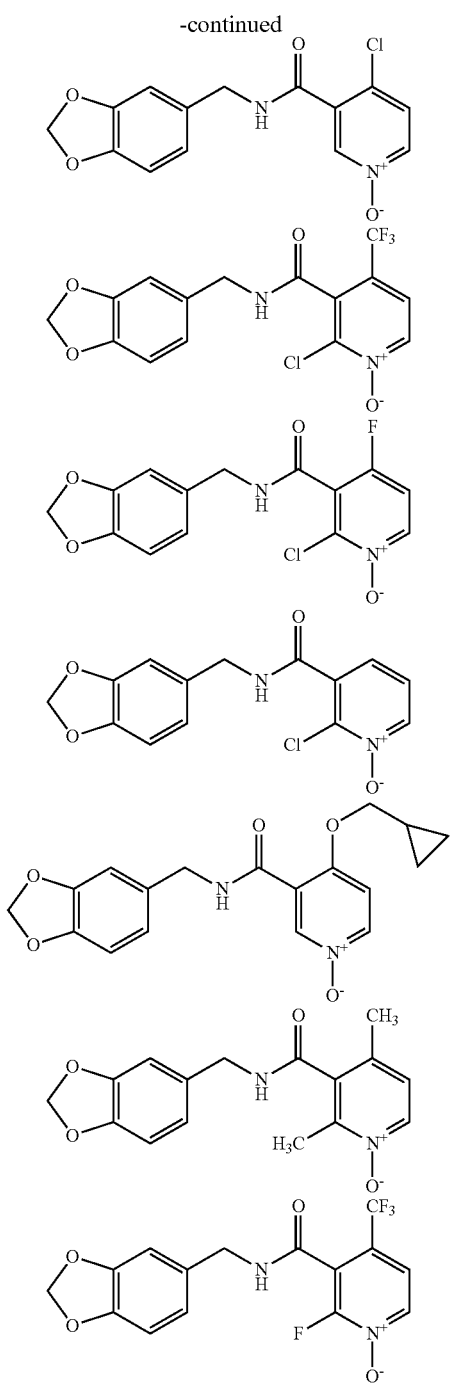

Whether a compound is an ALDH agonist can be readily ascertained. Assays for dehydrogenase activity of ALDH are known in the art, and any known assay can be used. Examples of dehydrogenase assays are found in various publications, including, e.g., Sheikh et al. ((1997) *J. Biol. Chem.* 272: 18817-18822); Vallari and Pietruszko (1984) *J. Biol. Chem.* 259:4922; and Farres et al. ((1994) *J. Biol. Chem.* 269:13854-13860).

As an example of an assay for dehydrogenase activity, ALDH aldehyde dehydrogenase activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and an aldehyde substrate such as 14 μM propionaldehyde. Reduction of $NAD^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213, and as depicted schematically in FIG. 4. In an exemplary assay, the reaction is carried out at 25° C. in 0.1 sodium pyrophosphate (NaPPi) buffer, pH 9.0, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213, and as depicted schematically in FIG. 4. Detection of fluorescent resorufin at 590 nm provides amplified and more sensitive signals for any change in ALDH aldehyde dehydrogenase enzymatic activity. $NADP^+$ can be used in place of $NAD^+$ in this assay. In some embodiments, a substrate other than the substrate depicted in FIG. 4 is used. Suitable substrates include, but are not limited to, octylaldehyde, phenylacetaldehyde, retinaldehyde, and 4-hydroxynonenal. Although the reaction depicted in FIG. 4 shows use of purified ALDH2, other ALDH polypeptides (e.g., ALDH1, ALDH3, ALDH5, etc.) can be used. The enzyme used in the assay can be purified (e.g., at least about 75% pure, at least about 80% pure, at least about 85% pure, at least about 90% pure, at least about 95% pure, at least about 98% pure, or at least about 99% pure). Recombinant ALDH enzyme can also be used in the assay.

As another example, the effect of a compound on aldehyde dehydrogenase activity of an ALDH polypeptide can be assayed as described in Wierzchowski et al. ((1996) *Analytica Chimica Acta* 319:209), in which a fluorogenic synthetic substrate, e.g., 7-methoxy-1-naphthaldehyde is used. For example, the reaction could include 7-methoxy-1-naphthaldehyde, $NAD^+$, an ALDH polypeptide, and an ALDH agonist to be tested; fluorescence (excitation, 330 nm; emission 390 nm) is measured as a readout of enzymatic activity.

Whether a compound increases an esterase activity of ALDH can be determined using any known assay for esterase activity. For example, esterase activity of ALDH2 can be determined by monitoring the rate of p-nitrophenol formation at 400 nm in 25 mM N,N-Bis(2-hydroxyethyl)-2-amino ethanesulfonic acid (BES) (pH 7.5) with 800 μM p-nitrophenyl acetate as the substrate at room temperature in the absence or presence of added $NAD^+$. A pH-dependent molar extinction coefficient of 16 $mM^{-1}$ $cm^{-1}$ at 400 nm for nitrophenol can be used. See, e.g., Larson et al. (2007) *J. Biol. Chem.* 282:12940). Esterase activity of ALDH can be determined by measuring the rate of p-nitrophenol formation at 400 nm in 50 mM Pipes (pH 7.4) with 1 mM p-nitrophenylacetate as the substrate. A molar extinction coefficient of $18.3 \times 10^3$ $M^{-1}$ $cm^{-1}$ at 400 nm for p-nitrophenolate can be used for calculating its rate of formation. See, e.g., Ho et al. (2005) *Biochemistry* 44:8022).

Whether a compound increases a reductase activity of ALDH can be determined using any known assay for reductase activity. A reductase activity of ALDH can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 ml in ethanol for subsequent TLC separation and scintillation counting. See, e.g., Zhang and Stamler (2002) *Proc. Natl. Acad. Sci. USA* 99:8306.

Pharmaceutical Compositions, Dosages, Routes of Administration

The present invention provides pharmaceutical compositions comprising a subject ALDH agonist. The terms "ALDH agonist" and "ALDH activator" are also referred to herein as "active agent." A subject ALDH agonist is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for a subject active agent depend on the particular compound employed and the effect to be achieved, and the pharmacodynamics associated with each compound in the host.

In the subject methods, a subject ALDH agonist may be administered to the host using any convenient means capable of resulting in the desired outcome, e.g., reduction of disease, reduction of a symptom of a disease, etc. Thus, a subject ALDH agonist can be incorporated into a variety of formulations for therapeutic administration. More particularly, a subject ALDH agonist can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In pharmaceutical dosage forms, a subject ALDH agonist ("active agent") may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, a subject active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject active agent can be utilized in aerosol formulation to be administered via inhalation. A subject active agent can be formulated into pressurized acceptable propellants such as dichlorodifluoromethane, propane, nitrogen and the like.

Furthermore, a subject active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

A subject active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Ocular Formulations

A subject active agent can be formulated for ocular delivery, e.g., where a subject active agent is formulated for delivery to the eye in liquid form (e.g., eye drops), or for injection into or around the eye.

A subject active agent can be formulated in an ophthalmic pharmaceutical composition. Ophthalmic pharmaceutical compositions can be adapted for topical administration to the eye in the form of solutions, suspensions, ointments, creams or as a solid insert. Ophthalmic formulations of comprising a subject active agent can contain from 0.01 to 5%, or from 0.1 to 2% of a subject active agent. Higher dosages as, for example, about 10% or lower dosages can be employed provided the dose is effective in treating a disorder of the eye (e.g., cataracts). For a single dose, from between 0.001 to 5.0 mg, e.g., from 0.005 to 2.0 mg, or from 0.005 to 1.0 mg of a subject active agent can be applied to the human eye.

A subject active agent can be conveniently admixed with a non-toxic pharmaceutical organic carrier, or with a non-toxic pharmaceutical inorganic carrier. Suitable pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation can also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitate, dioctyl sodium sulfosuccinate, monothioglycerol, thiosorbitol, ethylenediamine tetracetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation can also be in the form of a microparticle formulation. The pharmaceutical preparation can also be in the form of a solid insert. For example, one may use a solid water soluble polymer as the carrier for the medicament. The polymer used to form the insert can be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

A pharmaceutical preparation comprising a subject active agent can further include one or more non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

Topical Formulations

A subject active agent can be formulated for topical administration to the skin. For example, a subject active agent can be formulated with one or more dermatologically acceptable excipients.

The term "dermatologically acceptable," as used herein, means that the compositions or components thereof so described are suitable for use in contact with human skin without undue toxicity, incompatibility, instability, allergic response, and the like.

Suitable excipients include emollients; humectants; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and the like.

A variety of emollients may be employed to yield the conditioning component of the present invention. These emollients may be selected from one or more of the following classes: triglyceride esters that include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; wax esters such as beeswax, spermaceti, myristyl myristate, stearyl stearate; forming a mixture of ether esters; and vegetable waxes including, but not limited to, carnauba and candelilla waxes; and cholesterol fatty acid esters.

Humectants of the polyhydric alcohol-type are suitable for use. Typical polyhydric alcohols include polyalkylene glycols and more preferably alkylene polyols and their derivatives, including propylene glycol, dipropylene glycol, tripropylene glycol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin and mixtures thereof.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and mixtures thereof.

A composition comprising a subject active agent can include a dermatologically-acceptable hydrophilic diluent. Non-limiting examples of hydrophilic diluents are water, organic hydrophilic diluents such as lower monovalent alcohols (e.g., $C_1$-$C_4$ alcohols) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. A composition comprising a subject active agent can contain from about 60% to about 99.99% of a hydrophilic diluent.

A composition comprising a subject active agent can include a dermatologically acceptable carrier. An example of a suitable carrier is an emulsion comprising a hydrophilic phase comprising a hydrophilic component, e.g., water or other hydrophilic diluent, and a hydrophobic phase comprising a hydrophobic component, e.g., a lipid, oil or oily material. The hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions can comprise from about 1% to about 50% of the dispersed hydrophobic phase and from about 1% to about 98% of the continuous hydrophilic phase; water-in-oil emulsions can comprise from about 1% to about 98% of the dispersed hydrophilic phase and from about 1% to about 50% of the continuous hydrophobic phase.

A subject active agent can be formulated with common excipients, diluents, or carriers, and formed into lotions, creams, solutions, suspensions, powders, aerosols, emulsions, salves, ointments and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. A composition comprising a subject ALDH agonist can include thickening agents such as cellulose and/or cellulose derivatives. A composition comprising a subject ALDH agonist can include contain gums such as xanthan, guar or carbo gum or gum arabic, or alternatively poly(ethylene glycol)s, bentones and montmorillonites, and the like.

A composition comprising a subject ALDH agonist can further include one or more additional agents such as, for example, antioxidants, surfactants, preservatives, film-forming, keratolytic or comedolytic agents, perfumes, flavorings, and colorings. Antioxidants such as t-butylhydroquinone, butylated hydroxyanisole, butylated hydroxytoluene and α-tocopherol and its derivatives can be added.

Furthermore, composition comprising a subject ALDH agonist can further include one or more additional therapeutic agents, for example, anti-microbial agents, pain relievers, anti-inflammatory agents, and the like, depending, e.g., on the condition being treated.

Continuous Delivery

In some embodiments, a subject active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of a subject active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Oral Formulations

In some embodiments, a subject active agent is formulated for oral delivery to an individual in need of such an agent.

For oral delivery, a subject formulation comprising a subject active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, a subject active agent is formulated with one or more pharmaceutical excipients and coated with an enteric coating, as described in U.S. Pat. No. 6,346,269. For example, a solution comprising a subject active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for a subject active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include a subject active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include a subject active agent with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Trilayer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoyl-carnitine, and sodium salts of fatty acids); toxins (e.g., zonula occludens toxin); and the like.

Inhalational Formulations

A subject ALDH agonist will in some embodiments be administered to a patient by means of a pharmaceutical delivery system for the inhalation route. A subject ALDH agonist can be formulated in a form suitable for administration by inhalation. The inhalational route of administration provides the advantage that the inhaled drug can bypass the blood-brain barrier. The pharmaceutical delivery system is one that is suitable for respiratory therapy by delivery of a subject ALDH agonist to mucosal linings of the bronchi. This invention can utilize a system that depends on the power of a compressed gas to expel the subject ALDH agonist from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains a subject ALDH agonist, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

A subject ALDH agonist can also be formulated for delivery with a nebulizer, which is an instrument that generates very fine liquid particles of substantially uniform size in a gas. For example, a liquid containing the subject ALDH agonist is dispersed as droplets. The small droplets can be carried by a current of air through an outlet tube of the nebulizer. The resulting mist penetrates into the respiratory tract of the patient.

A powder composition containing a subject ALDH agonist, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. A subject ALDH agonist can be formulated in basically three different types of formulations for inhalation. First, a subject ALDH agonist can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, a subject ALDH agonist can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718, 222; and 5,660,166.

A subject ALDH agonist can be formulated into dry powder formulations. Such formulations can be administered by simply inhaling the dry powder formulation after creating an aerosol mist of the powder. Technology for carrying such out is described within U.S. Pat. No. 5,775,320 and U.S. Pat. No. 5,740,794.

Dosages and Dosing

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, a subject ALDH activity modulator can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 µg to about 1,000 µg or about 10,000 µg of subject compound in a blood sample taken from the individual being treated, about 24 hours after administration of the compound to the individual.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound(s) in a composition as a solution in sterile water, normal saline or another pharmaceutically acceptable carrier.

In some embodiments, multiple doses of a subject compound are administered. The frequency of administration of a subject compound ("active agent") can vary depending on any of a variety of factors, e.g., severity of the symptoms, etc. For example, in some embodiments, a subject compound is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, a subject compound is administered continuously.

The duration of administration of a subject compound, e.g., the period of time over which a subject compound is administered, can vary, depending on any of a variety of factors, e.g., patient response, etc. For example, a subject compound can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, a subject compound is administered for the lifetime of the individual.

Routes of Administration

A subject ALDH agonist is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, ocular, rectal, nasal, oral, and other enteral and parenteral routes of administration. Routes of administration may be combined, if desired, or adjusted depending upon the agent and/or the desired effect. The compound can be administered in a single dose or in multiple doses.

A subject active agent can be administered to a host using any available conventional methods and routes suitable for delivery of conventional drugs, including systemic or localized routes. In general, routes of administration contemplated by the invention include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of a subject ALDH agonist through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Treatment Methods

The present invention provides various treatment methods, generally involving administering to an individual in need thereof an effective amount of a subject agonist. A subject ALDH agonist is suitable for treating a variety of disorders, including, e.g., conditions involving ischemic stress, chronic free-radical associated diseases, acute free-radical associated diseases, insensitivity to nitroglycerin (e.g., in angina and heart failure), hypertension, cataracts, diabetes, and osteoporosis. A subject ALDH agonist is suitable for sensitizing a cancerous cell to a cancer chemotherapeutic agent or other standard cancer therapy; for treating alcohol (e.g., ethanol; ethyl alcohol) addiction; and for treating narcotic addiction.

Methods of Treating Conditions Involving Ischemic Stress

The present invention provides methods for treating conditions involving ischemic stress, including prophylactic methods, in an individual, the methods generally involving administering to an individual in need thereof an effective amount of a subject ALDH agonist. Conditions involving ischemic stress include ischemic conditions, ischemic events, conditions that can give rise to ischemia, and conditions that result from an ischemic event. Conditions involving ischemic stress that are amenable to treatment with a subject method include ischemia that result from any condition or event, including, but not limited to, myocardial infarct (e.g., acute myocardial infarction), cardiac surgery, brain trauma, cerebrovascular disease, stroke, spinal cord injury, subarachnoid hemorrhage, major surgery in which ischemia to variety of organs occur, organ transplantation, limb ischemia (e.g., resulting from Type 1 or Type 2 diabetes), and the like.

In some embodiments, the agent is administered before a predicted or anticipated ischemic event, e.g., from about 1 hour to about 1 week before the ischemic event, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 24 hours to about 36 hours, from about 36 hours to about 48 hours, from about 48 hours to about 72 hours, or from about 72 hours to about 1 week preceding the predicted or anticipated ischemic event.

Pretreatment with an active agent is desirable under certain circumstances, for example, when a subject has already experienced a stroke, when a subject is about to undergo cardiac surgery, etc. For example, a patient who has already experienced a stroke will have an increased probability of experiencing a second stroke. Subjects who are susceptible to transient ischemic attacks also have an increased risk of a stroke. Subjects who suffer a subarachnoid hemorrhage may experience further ischemic events induced by vasospasms that constrict the blood vessels. Subjects who experience trauma to organs such as the brain are also susceptible to an ischemic event. Subjects undergoing surgery over an extended period of time are also susceptible to an ischemic event. The above situations exemplify circumstances when a subject would benefit from pretreatment with a subject ALDH agonist.

In some embodiments, a subject ALDH agonist is administered after an ischemic event. For example, a subject ALDH agonist is effective in reducing the adverse effects of an ischemic event such as cardiac ischemia, reperfusion injury, cerebrovascular disease, acute myocardial infarction, subarachnoid hemorrhage, and trauma. In some embodiments, a subject ALDH agonist is administered within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the ischemic event. In some embodiments, an increased concentration of a subject ALDH2 agonist is maintained in the plasma for at least several hours to several days following the ischemic event.

For example, in some embodiments, a subject ALDH agonist is administered to an individual who has suffered an acute myocardial infarction (AMI) within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the AMI.

Methods of Treating Ocular Disorders

The present invention provides methods for treating ocular disorders, e.g., cataracts, the methods generally involving administering to an individual in need thereof an effective amount of a subject ALDH agonist. In some embodiments, the ALDH agonist will be an ALDH3 agonist. The ALDH agonist will be formulated for ocular administration, e.g., for topical administration to the eye, for injection into the eye (e.g., intravitreal injection), or some other route of administration to the eye. Ocular disorders that can be treated with a subject ALDH agonist include, e.g., age-related cataracts, secondary cataracts, traumatic cataracts, congenital cataracts, radiation cataracts, etc.

Among the risk factors for cataract are exposure to UV-light (which can result in generation of toxic aldehydes such as 4-hydroxy-2-nonenal), exposure to cigarette smoke (cigarette smoke contains high amounts of reactive aldehydes, such as acrolein). See, e.g., Jia et al., Invest Ophthalmol Vis Sci. 2007 January; 48(1):339-48. PMID: 17197552; J Dong et al., Neurochem. 2007 November; 103(3):1041-52. PMID: 17935603; Papa et al., Free Radic Biol Med. 2003 May 1; 34(9):1178-89. PMID: 12706498; King et al. J Exp Zool. 1998 Sep.-Oct. 1; 282(1-2):12-7. PMID: 9723161). The instant disclosure provides methods of treating cataracts, the methods generally involving administering to an individual in need thereof an effective amount of an ALDH agonist, e.g., a subject ALDH agonist.

A subject ALDH agonist can be administered to an individual in need thereof for the treatment of an ocular disorder (e.g., cataracts), where the ALDH agonist is administered topically to the eye, e.g., in the form of eyedrops.

A subject ALDH agonist can be administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), for the treatment of an ocular disorder. A subject ALDH agonist can be administered over a period of time of from about 3 months to about 1 year, from 1 year to 10 years, or more than 10 years.

In some embodiments, where a subject ALDH agonist is administered for the treatment of cataracts, the ALDH agonist is administered before or after surgery for cataracts.

Methods of Treating Skin Disorders

The present invention provides methods for treating skin disorders, the methods generally involving administering to an individual in need thereof an effective amount of a subject ALDH agonist.

Skin disorders that can be treated with a subject ALDH agonist include, but are not limited to, dermatitis. In some embodiments, for the treatment of a skin disorder, a subject ALDH agonist is administered topically to the skin, e.g., to an area of skin affected by a skin disorder.

Methods of Treating Chronic and Acute Free-Radical Associated Diseases

The present invention provides methods for treating acute and chronic free-radical associated diseases in an individual, the methods generally involving administering to an individual in need thereof an effective amount of a subject ALDH agonist.

Acute Free-Radical Associated Disorders

The present invention provides methods for treating acute free-radical associated diseases in an individual, the methods generally involving administering to an individual in need thereof an effective amount of a subject ALDH agonist. Acute free radical-associated disorders that are amenable to treatment with a subject method include seizures (Patel et al. (2001) *Journal of Neurochemistry* 79:1065-1069); skin damage resulting from UV exposure, and photodamage of skin (e.g., "sunburn") (Aldini et al. (2007) *Chem Res Toxicol.* 20(3):416-23); acute thermal skin burn injury (Pintaudi et al. (2000) *Free Radical Res.* 33(2):139-46); and tissue hyperoxia (e.g., hyperoxia-induced chronic lung disease; and bronchopulmonary dysplasia) (Xu et al. (2006) *Am J. Phsiol. Lung Cell. Mol. Physiol.* 291(5):L966-75).

The present invention provides methods for treating sunburn in an individual, the methods generally involving administering to an individual in need thereof an effective amount of a subject ALDH agonist. In some embodiments, a subject method for treating sunburn comprises topically applying a formulation comprising a subject ALDH agonist to an area of the skin affected by sunburn.

The present invention provides methods for treating a seizure in an individual, the methods generally involving administering to an individual in need thereof an effective amount of a subject ALDH agonist. In some embodiments, a subject ALDH agonist is administered after a seizure has occurred, e.g., within from about 1 minute to about 5 minutes, from about 5 minutes to about 15 minutes, from about 15 minutes to about 30 minutes, from about 30 minutes to about 1 hour, or from about 1 hour to about 4 hours following a seizure. In other embodiments, a subject ALDH agonist is administered prophylactically, e.g., a subject ALDH agonist is administered to an individual who has experienced a seizure in the past, to reduce the likelihood that another seizure will occur. In some embodiments, an effective amount of a subject ALDH agonist is an amount that is effective to reduce at least one of the severity of a seizure, the frequency of seizures, and the duration of a seizure.

Chronic Free-Radical Associated Diseases

The present invention provides methods for treating chronic free-radical associated diseases in an individual, the methods generally involving administering to an individual in need thereof an effective amount of a subject ALDH agonist. Chronic free radical-associated disorders that are amenable to treatment with a subject method include neurodegenerative diseases such as Parkinson's Disease and Alzheimer's Disease (Burke et al. (2003) *Neurol. Dis.* 2(2):143; and Ohta and Ohsawa (2006) *J. Alzheimer's Disease* 9(2):155); amyotrophic lateral sclerosis (ALS); cancer such as esophageal cancer (Chen et al. (2006) *Int J Cancer* 2119(12):2827-31); upper aerodigestive tract cancer (Hashibe et al. (2006) *Cancer Epidemiol Biomarkers Prev.* 15(4):696-703); head and neck squamous cell carcinoma (Hashimoto et al. (2006) *Tumour Biol.* 27(6):334-8; Yokoyama et al. (2005) *Alcohol.* 35(3):175-85); cardiovascular diseases such as atherosclerosis (Narita et al. (2003) *Ultrasound in Medicine and Biology* 29(10):1415-1419); and the like. In some embodiments, a chronic free radical-associated disease is treated by chronic (e.g., daily) treatment with a subject ALDH agonist.

The present invention provides a method for treating Alzheimer's Disease (AD) in an individual suffering from AD, the method generally involving administering to the individual an effective amount of a subject ALDH agonist. In some embodiments, an "effective amount" of a subject ALDH agonist is an amount that is effective to at least slow the decline in cognitive function in the individual. In some embodiments, an "effective amount" of a subject ALDH agonist is an amount that is effective to improve memory in the individual being treated. In some embodiments, a subject ALDH agonist is administered to the individual systemically, over a period of time of from about 3 months to about 6 months, from about 6 months to about 1 year, or more than 1 year.

The present invention provides a method for treating Parkinson's Disease in an individual, the method generally involving administering to the individual an effective amount of a subject ALDH agonist. In some embodiments, an "effective amount" of a subject ALDH agonist is an amount that is effective to ameliorate one or more symptoms of Parkinson's Disease. In some embodiments, an "effective amount" of a subject ALDH agonist is an amount that is effective to slow the progress of the disease. In some embodiments, a subject ALDH agonist is administered to the individual systemically, over a period of time of from about 3 months to about 6 months, from about 6 months to about 1 year, or more than 1 year.

Methods of Treating Heart Conditions

The present invention provides methods of treating disorders such as angina, heart failure, insensitivity to nitroglycerin in angina and heart failure (Li et al. (2006) *J. Clin. Invest.* 116:506-511), hypertension (Asselin et al. (2006) *Free Radical Biol. and Med.* 41:97), and heart disease. The methods generally involve administering to an individual in need thereof an effective amount of a subject ALDH agonist.

In some embodiments, a subject ALDH agonist is administered to an individual in conjunction with nitroglycerin treatment. The subject ALDH agonist and the nitroglycerin can be administered by the same route of administration (e.g., oral, sublingual, transdermal, translingual, etc.). In the alternative, subject ALDH agonist and the nitroglycerin can be administered by different routes of administration. For example, in some embodiments, nitroglycerin is administered sublingually, translingually, transdermally, or orally; and a subject ALDH agonist is administered via a different route of administration (e.g., intravenous, intramuscular, etc.). The ALDH agonist can be administered before, during, or after administration of the nitroglycerin.

An effective amount of a subject ALDH agonist is an amount that, when administered in combination therapy with nitroglycerin, is effective to reduce angina by at least about 10%, at least about 20%, at least about 30%, at least about 40%, at least about 50%, at least about 60%, at least about 70%, at least about 80%, or at least about 90%, or more, within a period of time of from about 1 minute to about 2 minutes, from about 2 minutes to about 3 minutes, from about 3 minutes to about 4 minutes, from about 4 minutes to about 5 minutes, or from about 5 minutes to about 10 minutes, following administration of the ALDH agonist. In some embodiments, a subject ALDH agonist and nitroglycerin are administered substantially simultaneously, e.g., within about two minutes, within about 1 minute, or within about 30 seconds of one another. The term "combination therapy with nitroglycerin" encompasses administration of a subject ALDH agonist substantially simultaneously with nitroglycerin; administration of a subject ALDH agonist before administration of nitroglycerin; administration of a subject ALDH agonist after administration of nitroglycerin; etc.

In some embodiments, an effective amount of a subject ALDH agonist is an amount that is effective to treat hypertension, e.g., to reduce one or more symptoms or indications of hypertension in an individual. For example, in some embodiments, an effective amount of a subject ALDH agonist is an amount that is effective to reduce blood pressure in the individual by at least about 5%, at least about 10%, at least about 15%, at least about 20%, or at least about 25%, or more, or to bring the blood pressure of the individual to within a normal range.

In some embodiments, an effective amount of a subject ALDH agonist is an amount that is effective to treat heart disease, e.g., to reduce one or more symptoms or indications of heart disease in an individual. Whether a given ALDH agonist is effective to treat heart disease can be determined using standard methods of assessing heart function, e.g., electrocardiogram, angiogram, and the like.

Methods of Detoxification

The present invention provides methods of reducing the levels of a toxic compound in an individual, the methods generally involving administering to an individual in need thereof an effective amount of a subject ALDH agonist. The present invention provides methods of treating a disorder associated with or resulting from a toxic level of a compound (e.g., a xenogenic aldehyde; a biogenic aldehyde; or a compound that, when ingested, absorbed, or inhaled, gives rise to an aldehyde substrate for ALDH), the methods generally involving administering to an individual in need thereof an effective amount of a subject ALDH agonist, where the level of the compound in the individual is reduced to a non-toxic level.

Toxic compounds whose levels can be reduced in an individual using a subject method include, but are not limited to, ethanol, methanol, ethylene glycol monomethyl ether, xenogenic aldehydes, biogenic aldehydes, and an aldehyde produced by in vivo metabolism of a compound that is ingested, absorbed, or inhaled. A subject ALDH agonist is administered in an amount that is effective, when administered in one or more doses, to reduce a toxic level of a compound such as ethanol, methanol, ethylene glycol monomethyl ether, xenogenic aldehydes, biogenic aldehydes, or an aldehyde produced by in vivo metabolism of a compound that is ingested, absorbed, or inhaled. In some embodiments, the aldehyde is acetaldehyde.

As an example, a subject ALDH agonist is administered to an individual following excessive alcohol (e.g., ethanol) consumption; and toxic levels of alcohol or aldehyde (e.g., an aldehyde that is a metabolic product of ethanol) in the individual are reduced by at least about 10%, at least about 20%, at least about 30%, at least about 40%, at least about 50%, at least about 60%, at least about 70%, at least about 80%, or at least about 90%, or more, compared to the alcohol or aldehyde levels in the individual before treatment with the ALDH agonist. In some embodiments, a subject ALDH agonist is administered in an amount that is effective to reduce a toxic alcohol or aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic alcohol or aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

As an example, a subject ALDH agonist is administered to an individual following excessive alcohol (e.g., ethanol) consumption; and levels of acetaldehyde in the individual are reduced by at least about 10%, at least about 20%, at least about 30%, at least about 40%, at least about 50%, at least about 60%, at least about 70%, at least about 80%, or at least about 90%, or more, compared to the alcohol or aldehyde levels in the individual before treatment with the ALDH agonist. In some embodiments, a subject ALDH agonist is administered in an amount that is effective to reduce an acetaldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

The present invention provides methods of reducing aldehyde toxicity, the methods generally involving administering an effective amount of a subject ALDH agonist. In some embodiments, an effective amount of an ALDH agonist is an amount that is effective to reduce one or more symptoms of aldehyde toxicity. For example, in some embodiments, an effective amount of an ALDH agonist is an amount that is effective to reduce one or more symptoms of excess ethanol consumption, where such symptoms include, e.g., headache, dehydration, fatigue, nausea, vomiting, diarrhea, weakness, anxiety, irritability, photophobia, phonophobia, etc.

As an example, a subject ALDH agonist is administered to an individual having a toxic level of an aldehyde (e.g., following excessive ethanol consumption); and toxic levels of an aldehyde in the individual are reduced by at least about 10%, at least about 20%, at least about 30%, at least about 40%, at least about 50%, at least about 60%, at least about 70%, at least about 80%, or at least about 90%, or more, compared to the level of the aldehyde in the individual before treatment with the ALDH agonist. In some embodiments, a subject ALDH agonist is administered in an amount that is effective to reduce a toxic aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

In some embodiments, a subject ALDH agonist reduces the level of both ethanol and an aldehyde, e.g., following excessive ethanol consumption, as described above.

As another example, a subject ALDH agonist is administered to an individual having toxic levels of methanol or ethylene glycol monomethyl ether; and the toxic level of methanol or ethylene glycol monomethyl ether is reduced by at least about 10%, at least about 20%, at least about 30%, at least about 40%, at least about 50%, at least about 60%, at least about 70%, at least about 80%, or at least about 90%, or more, compared to the methanol or ethylene glycol monomethyl ether level in the individual before treatment with the ALDH agonist. In some embodiments, a subject ALDH agonist is administered in an amount that is effective to reduce a toxic methanol or ethylene glycol monomethyl ether level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic methanol or ethylene glycol monomethyl ether level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

As another example, a subject ALDH agonist is administered to an individual exhibiting drug toxicity, e.g., a toxic level of an aldehyde following ingestion, absorption, or inhalation of a drug (e.g., a pharmaceutical compound, an illicit drug, etc.). In some embodiments, the aldehyde is produced following ingestion, absorption, or inhalation of a drug, by metabolism of the drug in the body. The toxic level of aldehyde is reduced by at least about 10%, at least about 20%, at least about 30%, at least about 40%, at least about 50%, at least about 60%, at least about 70%, at least about 80%, or at least about 90%, or more, compared to the level of the aldehyde in the individual before treatment with the ALDH agonist. In some embodiments, a subject ALDH agonist is administered in an amount that is effective to reduce a toxic aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

Methods of Reducing Salsolinol Levels

The present invention provides methods of reducing salsolinol levels in an individual, the methods generally involving administering to the individual an effective amount of a subject ALDH agonist. Salsolinol (1-methyl-6,7-dihydroxy-1,2,3,4-tetrahydroisoquionoline) is a condensation product of dopamine with acetaldehyde. Acetaldehyde is a metabolic product of ethanol. Plasma salsolinol levels are higher in alcoholic compared to non-alcoholics. Reduction of salsolinol levels is useful in reducing alcohol addiction.

In some embodiments, an effective amount of a subject ALDH agonist is administered to an individual in need thereof following excessive alcohol (e.g., ethanol) consumption; where the effective amount provides for a reduction in the levels of salsolinol in the individual of at least about 10%, at least about 20%, at least about 30%, at least about 40%, at least about 50%, at least about 60%, at least about 70%, at least about 80%, or at least about 90%, or more, compared to the salsolinol levels in the individual before treatment with the ALDH agonist. In some embodiments, an effective amount of a subject ALDH agonist is administered to an individual in need thereof at any time (e.g., not necessarily following excessive alcohol consumption). In some embodiments, a subject ALDH agonist is administered in an amount that is effective to reduce a salsolinol level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some of these embodiments, the individual is one who has been diagnosed with alcoholism. Symptoms and diagnosis of alcoholism are described in, e.g., Enoch and Goldman (2002) *American Family Physician* 65:441.

Methods of Treating Diabetes

The present invention provides methods of treating diabetes, the methods generally involving administering to an individual in need thereof an effective amount of a subject ALDH agonist. In some embodiments, a subject method of treating diabetes provides for treatment of a disorder that is a result of diabetes, e.g., diabetic nephropathy, diabetic neuropathy, and the like.

In some embodiments, a subject ALDH agonist is administered in an amount that is effective to reduce a blood glucose level in an individual, e.g., to reduce a blood glucose level in an individual by at least about 10%, at least about 15%, at least about 20%, at least about 25%, at least about 30%, at least about 40%, or at least about 50% when compared to the blood glucose levels in the absence of treatment with the agonist. In some embodiments, an effective amount of an ALDH agonist is an amount that is effective to reduce blood glucose levels to a normal range. Normal fasting blood glucose levels are typically in the range of from about 70 mg/dL to about 110 mg/dL before a meal. Normal blood glucose levels 2 hours after a meal are usually less than about 120 mg/dL. Normal blood glucose levels during an oral glucose tolerance test (involving drinking a sugar solution containing about 75 g glucose; then measuring blood glucose levels at various times following drinking the sugar solution) include: less than 140 mg/dL 2 hours after drinking the sugar solution; and all readings between 0 and 2 hours after drinking the sugar solution less than 200 mg/dL. Blood glucose levels are also sometimes expressed in mmol/L. Normal blood glucose levels are generally between about 4 mmol/L and 8 mmol/L. Normal blood glucose levels are generally less than about 10 mmol/L 90 minutes after a meal; and from about 4 mmol/L to about 7 mmol/L before meals.

In some embodiments, a subject treatment method comprises administering a subject ALDH agonist, and co-administering at least a second therapeutic agent (e.g., insulin) for the treatment of diabetes. Insulin that is suitable for use herein includes, but is not limited to, regular insulin, semilente, NPH, lente, protamine zinc insulin (PZI), ultralente, insuline glargine, insulin aspart, acylated insulin, monomeric insulin, superactive insulin, hepatoselective insulin, and any other insulin analog or derivative, and mixtures of any of the foregoing. Insulin that is suitable for use herein includes, but is not limited to, the insulin forms disclosed in U.S. Pat. Nos. 4,992,417; 4,992,418; 5,474,978; 5,514,646; 5,504,188; 5,547,929; 5,650,486; 5,693,609; 5,700,662; 5,747,642; 5,922,675; 5,952,297; and 6,034,054; and published PCT applications WO 00/121197; WO 09/010645; and WO 90/12814. Insulin analogs include, but are not limited to, superactive insulin analogs, monomeric insulins, and hepatospecific insulin analogs.

Methods of Treating Osteoporosis

The present invention provides methods of treating osteoporosis, the methods generally involving administering to an individual in need thereof an effective amount of a subject ALDH agonist. In some embodiments, an "effective amount" of an ALDH agonist is an amount effective to increase bone density in the individual. In other embodiments, an "effective amount" of an ALDH agonist is an amount that is effective to reduce the rate of bone density loss.

Subjects Suitable for Treatment

Subjects suitable for treatment with a subject ALDH agonist include individuals suffering from a condition described above; individuals at risk for developing a condition described above; individuals who have been treated for a condition described above with an agent other than a subject ALDH agonist, and who either failed to respond to such treatment, or who initially responded to such treatment, but subsequently relapsed; individuals who are refractory to treatment with an agent other than a subject ALDH agonist for a condition described above; and individuals who cannot tolerate treatment with an agent other than a subject ALDH agonist for a condition described above. Subjects suitable for treatment with a subject compound include individuals who have been diagnosed with a condition as discussed above.

Methods Involving Administering an ALDH Agonist

A subject treatment method involving administration of a subject ALDH agonist is suitable for treating various conditions, as noted above, including disorders or conditions associated with or resulting from oxidative stress; disorders or conditions associated with nitroglycerin insensitivity; disorders or conditions associated with toxic levels of ethyl alcohol, aldehyde, methanol, ethylene glycol monomethyl ether, biogenic or xenogenic aldehydes, etc.; and heart diseases and conditions, such as coronary artery disease, angina, etc. In some embodiments, the individual is a human who is homozygous for an ALDH2 allele that encodes an ALDH2 having an amino acid sequence as depicted in FIG. 1A. In other embodiments, the individual is a human who carries one or two ALDH2*2 alleles, where an ALDH2*2 allele encodes an ALDH2 having the E487K variant as depicted in FIG. 1B.

Approximately 40% of the East Asian population carries the semidominant ALDH2*2 allele. Such individuals can be characterized by a response to ethanol consumption that includes one or more of facial flushing, nausea, and tachycardia. In addition, ALDH2*2 individuals are also less responsive to nitroglycerin treatment for such disorders as angina and coronary artery disease. Individuals who are heterozygous or homozygous for the ALDH2*2 allele are suitable for treatment with a subject method involving administration of a subject ALDH agonist.

Methods of Treating Conditions Associated with Ischemic Stress

Subjects suitable for treatment with subject ALDH agonist include individuals who are scheduled to undergo cardiac surgery or who have undergone cardiac surgery; individuals who have experienced a stroke; individuals who have suffered brain trauma; individuals who have prolonged surgery; individuals who have suffered a myocardial infarct (e.g., acute myocardial infarction); individuals who suffer from cerebrovascular disease; individuals who have spinal cord injury; individuals having a subarachnoid hemorrhage; and individuals who will be subjected to organ transplantation. Subjects suitable for treatment with a subject ALDH agonist also include individuals having an ischemic limb disorder, e.g., resulting from Type 1 or Type 2 diabetes.

Methods of Treating Acute Free-Radical Associated Diseases

Subjects suitable for treatment with subject ALDH agonist include individuals who are having or who have experienced a seizure; individuals having skin damage resulting from UV exposure; individuals having photodamage of the skin; individuals having an acute thermal skin burn injury; and individuals suffering from tissue hyperoxia.

Methods of Treating Chronic Free-Radical Associated Diseases

Subjects suitable for treatment with subject ALDH agonist include individuals who have been diagnosed with Alzheimer's disease, Parkinson's disease, amyotrophic lateral sclerosis, or other neurodegenerative disease; individuals having atherosclerosis; individuals having esophageal cancer; individuals having head and neck squamous cell carcinoma; and individuals having upper aerodigestive tract cancer.

Methods of Treating Cardiac Conditions

Subjects suitable for treatment with a subject ALDH agonist include individuals having angina; individuals having heart failure; individuals who exhibit an insensitivity to nitroglycerin in the treatment of angina or heart failure; individuals having hypertension; and individuals having heart disease.

Detoxification Methods

Subjects suitable for treatment with a subject ALDH agonist include individuals who have toxic levels of an aldehyde, e.g., via ingestion of a toxic compound, via inhalation of a toxic compound, via ingestion or inhalation of toxic levels of a compound, or via production of the aldehyde during normal metabolism. Such individuals include, but are not limited to, individuals who have ingested or inhaled ethanol, methanol, ethylene glycol monomethyl ether, or other xenogenic or biogenic aldehyde compounds. For example, such individuals include individuals who have ingested or inhaled pesticides, fungicides, or other such compounds; individuals who have consumed excessive levels of ethanol; and the like.

Methods of Treating Diabetes

Subjects suitable for treatment with a subject ALDH agonist include individuals having Type 1 or Type 2 diabetes. Subjects suitable for treatment include individuals who have been diagnosed with Type 1 diabetes mellitus, where such individuals include those having a fasting blood glucose level greater than about 126 mg/dL. Such individuals include those having blood glucose levels of greater than about 200 mg/dL following a two-hour glucose tolerance test (75 g anhydrous glucose orally). Subjects suitable for treatment include individuals who have been diagnosed with Type 2 diabetes; individuals who have not yet been diagnosed with Type 2 diabetes, but who are at risk of developing Type 2 diabetes, e.g., individuals having a body mass index (weight in kilograms divided by height (in meters) squared) greater than 25, e.g., individuals having a body mass index from about 25 to about 27, from about 27 to about 30, or greater than 30.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an ALDH-mediated disorder selected from alcohol intolerance, alcohol addiction, alcohol abuse disorder, methanol poisoning, and ethylene glycol monomethyl ether poisoning, the method comprising administering to individual in need thereof a compound Formula I:

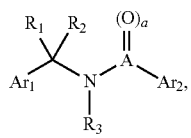

wherein:

each of $R_1$, $R_2$, and $R_3$ is independently selected from H, a halo, a substituted or unsubstituted phenyl group, an aliphatic group, an alkyl group, a substituted alkyl group, an alkenyl group, an alkynyl group, a substituted or unsubstituted cyclic group, a substituted or unsubstituted heterocyclic group, a substituted or unsubstituted aryl group, and a substituted or unsubstituted heteroaryl group;

A is C or S, wherein a=1 when A=C, and a=2 when A=S;

$Ar_1$ is selected from a substituted heterocyclic group, an unsubstituted heterocyclic group, a substituted aryl group, an unsubstituted aryl group, a substituted heteroaryl group, and an unsubstituted heteroaryl group; and $Ar_2$ is a substituted pyridine oxide;

or a pharmaceutically acceptable salt, an analog, or a derivative thereof.

2. The method of claim 1, wherein $Ar_1$ is:

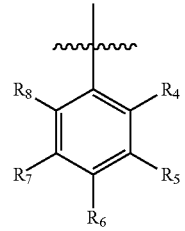

wherein $R_4$-$R_8$ are each independently selected from H, a halo, a substituted or unsubstituted phenyl group, an aliphatic group, an alkyl group, a substituted alkyl group, an alkenyl group, an alkynyl group, a substituted or unsubstituted cyclic group, a substituted or unsubstituted heterocyclic group, a substituted or unsubstituted aryl group, and a substituted or unsubstituted heteroaryl group.

3. The method of claim 1, wherein $Ar_1$ is a substituted or unsubstituted heterocyclic group.

4. The method claim 1, wherein the substituted pyridine oxide is selected from:

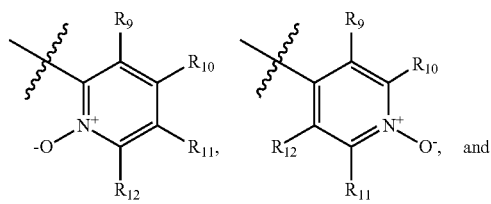

-continued

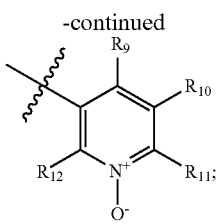

and

R_9 to R_12 are each independently selected from H, a halo, an aliphatic group, an alkyl group, a substituted alkyl group, an alkenyl group, an alkynyl group, a substituted or unsubstituted cyclic group, an ether, a substituted or unsubstituted amine, an ester, and an amide group.

5. The method of claim 1, wherein the compound is of Formula Ia:

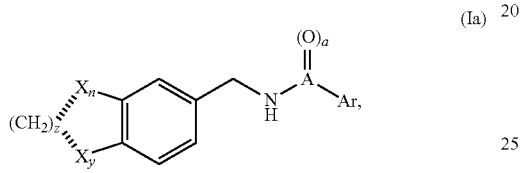 (Ia)

wherein:
$X_n$ and $X_y$ are each independently H, C, N, O, or a halogen;
... (dotted line) is an optional bond;
z is the integer 0, 1, or 2, with the provisos that: 1) z=0 when X=halogen and ... is not a bond; and 2) when z=0, X=O, is not a bond, and one or more oxygen atoms (X) are present, oxygen is attached to a methyl group;
n is the integer 0 or 1;
y is the integer 0 or 1;
A=C or S, wherein a=1 when A=C, and a=2 when A=S;
Ar is a substituted pyridine oxide of a formula selected from:

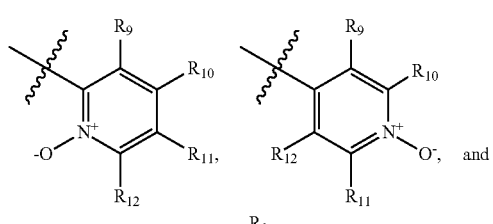

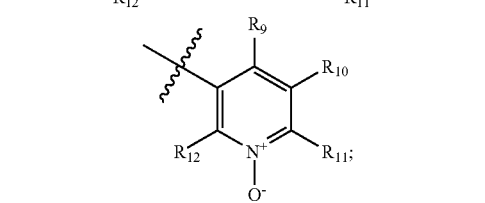

and

R_9 to R_12 are each independently selected from H, a halo, an aliphatic group, an alkyl group, a substituted alkyl group, an alkenyl group, an alkynyl group, a substituted or unsubstituted cyclic group, an ether, a substituted or unsubstituted amine, an ester, and an amide group;

or a pharmaceutically acceptable salt, an analog, or a derivative thereof.

6. The method of claim 1, wherein the compound is of Formula II:

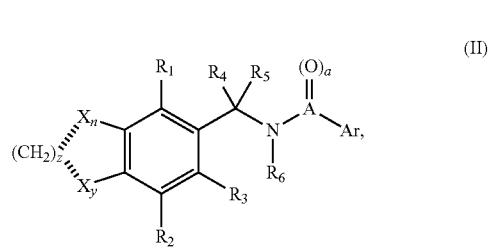 (II)

wherein:
$X_n$ and $X_y$ are each independently H, C, N, O, or a halogen;
n is the integer 0 or 1;
y is the integer 0 or 1;
... (dotted line) is an optional bond;
z is the integer 0, 1, or 2;
A is C or S, wherein a=1 when A=C, and a=2 when A=S;
Ar is a substituted pyridine oxide; and
R_1 to R_6 are each independently selected from H, a halo, a substituted or unsubstituted phenyl group, an aliphatic group, an alkyl group, a substituted alkyl group, an alkenyl group, an alkynyl group, a substituted or unsubstituted cyclic group, a substituted or unsubstituted heterocyclic group, a substituted or unsubstituted aryl group, and a substituted or unsubstituted heteroaryl group;

or a pharmaceutically acceptable salt, an analog, or a derivative thereof.

7. The method of claim 6, wherein the substituted pyridine oxide is of a formula selected from:

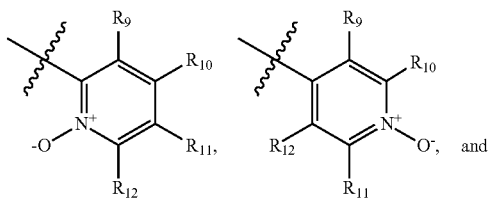

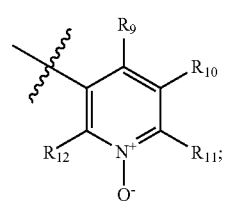

and

R_9 to R_12 are each independently selected from H, a halo, an aliphatic group, an alkyl group, a substituted alkyl group, an alkenyl group, an alkynyl group, a substituted or unsubstituted cyclic group, an ether, a substituted or unsubstituted amine, an ester, and an amide group.

8. The method of claim 1, wherein the compound is of Formula a:

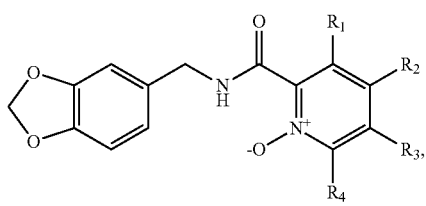

wherein $R_1$ to $R_4$ are each independently selected from H, a halo, an aliphatic group, an alkyl group, a substituted alkyl group, an alkenyl group, an alkynyl group, a substituted or unsubstituted cyclic group, an ether, a substituted or unsubstituted amine, an ester, and an amide group;

or a pharmaceutically acceptable salt, an analog, or a derivative thereof.

9. The method of claim 8, wherein the compound has a structure selected from:

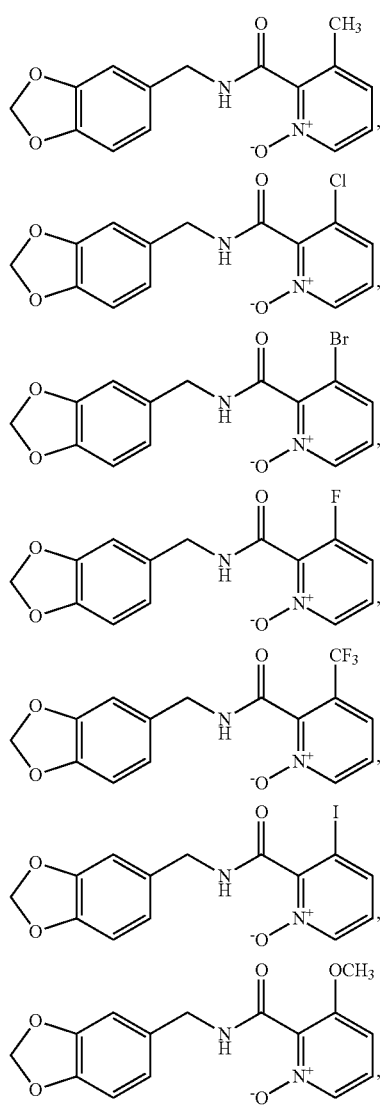

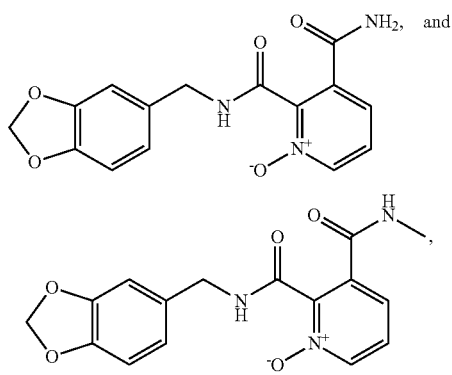

or a pharmaceutically acceptable salt, an analog, or a derivative thereof.

10. The method of claim 1, wherein the compound is of Formula b:

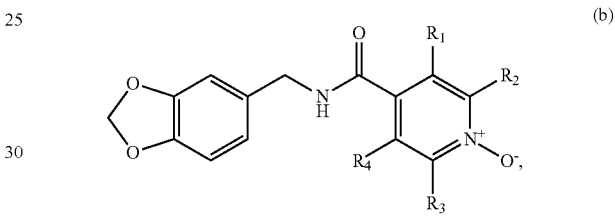

wherein $R_1$ to $R_4$ are each independently selected from H, a halo, an aliphatic group, an alkyl group, a substituted alkyl group, an alkenyl group, an alkynyl group, a substituted or unsubstituted cyclic group, an ether, a substituted or unsubstituted amine, an ester, and an amide group;

or a pharmaceutically acceptable salt, an analog, or a derivative thereof.

11. The method of claim 10, wherein the compound has a structure selected from:

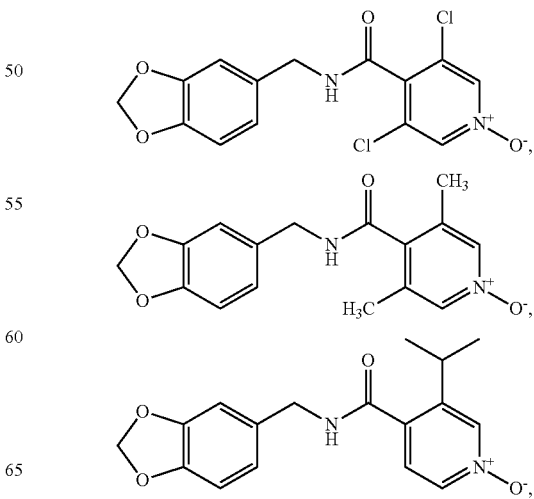

-continued

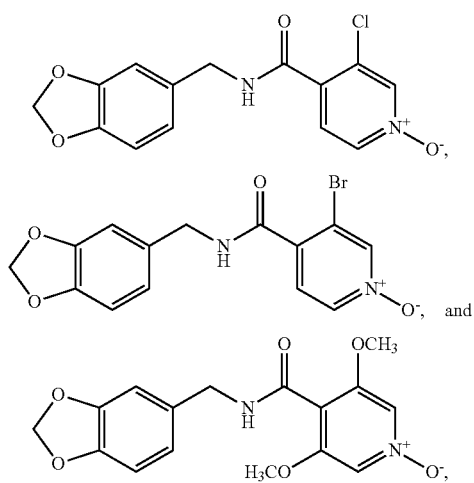

or a pharmaceutically acceptable salt, an analog, or a derivative thereof.

12. The method of claim 1, wherein the compound is of Formula c:

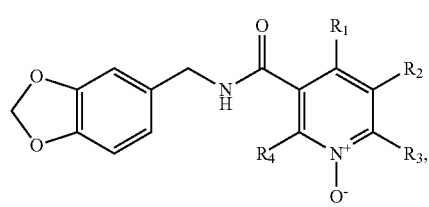

wherein $R_1$ to $R_4$ are each independently selected from H, a halo, an aliphatic group, an alkyl group, a substituted alkyl group, an alkenyl group, an alkynyl group, a substituted or unsubstituted cyclic group, an ether, a substituted or unsubstituted amine, an ester, and an amide group;

or a pharmaceutically acceptable salt, an analog, or a derivative thereof.

13. The method of claim 12, wherein the compound has a structure selected from:

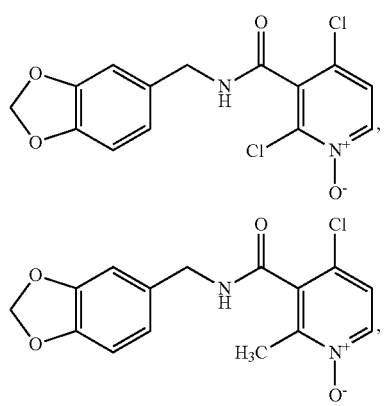

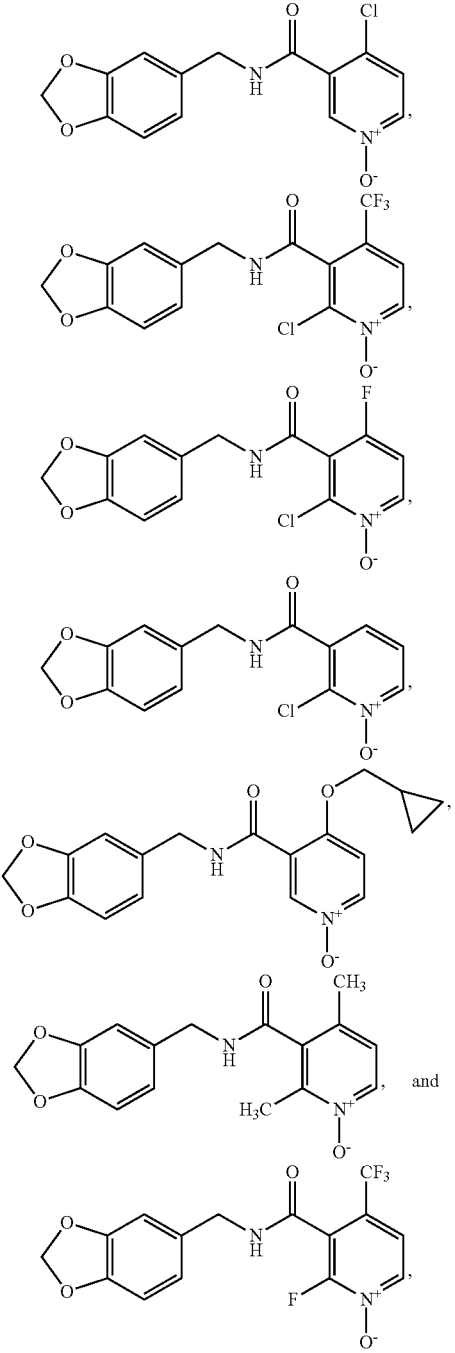

or a pharmaceutically acceptable salt, an analog, or a derivative thereof.

14. The method of claim 1, wherein the compound is present in a pharmaceutical composition comprising the compound and a pharmaceutically acceptable excipient.

15. The method of claim 1, wherein the compound is administered by a route selected from intramuscular, intravenous, subcutaneous, and oral.

16. The method of claim 1, wherein the individual has an ALDH2*2 allele.

17. The method of claim 14, wherein the pharmaceutical composition administered by a route selected from intramuscular, intravenous, subcutaneous, and oral.

18. The method of claim 14, wherein the individual has an ALDH2*2 allele.

19. The method of claim 3, wherein $Ar_1$ is selected from a substituted or unsubstituted pyridine, a thiazole, an imidazole, a thiophene, a quinoline, an isoquinoline, and a furan group.

* * * * *

SEQUENCE LISTING

```
<160> NUMBER OF SEQ ID NOS: 5

<210> SEQ ID NO 1
<211> LENGTH: 517
<212> TYPE: PRT
<213> ORGANISM: Homo sapiens

<400> SEQUENCE: 1

Met Leu Arg Ala Ala Ala Arg Phe Gly Pro Arg Leu Gly Arg Arg Leu
 1               5                  10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
        35                  40                  45

Val Ser Arg Lys Thr Phe Pro Thr Val Asn Pro Ser Thr Gly Glu Val
    50                  55                  60
```

-continued

```
Ile Cys Gln Val Ala Glu Gly Asp Lys Glu Val Asp Lys Ala Val
 65                  70                  75                  80

Lys Ala Ala Arg Ala Ala Phe Gln Leu Gly Ser Pro Trp Arg Arg Met
                 85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285

Lys Ser Pro Asn Ile Ile Met Ser Asp Ala Asp Met Asp Trp Ala Val
    290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
        355                 360                 365

Lys Ile Leu Gly Tyr Ile Asn Thr Gly Lys Gln Glu Gly Ala Lys Leu
    370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
        435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
```

```
                        485                 490                 495
Tyr Gly Leu Gln Ala Tyr Thr Glu Val Lys Thr Val Thr Val Lys Val
                500                 505                 510
Pro Gln Lys Asn Ser
        515

<210> SEQ ID NO 2
<211> LENGTH: 517
<212> TYPE: PRT
<213> ORGANISM: Homo sapiens

<400> SEQUENCE: 2

Met Leu Arg Ala Ala Ala Arg Phe Gly Pro Arg Leu Gly Arg Arg Leu
 1               5                  10                  15

Leu Ser Ala Ala Ala Thr Gln Ala Val Pro Ala Pro Asn Gln Gln Pro
                20                  25                  30

Glu Val Phe Cys Asn Gln Ile Phe Ile Asn Asn Glu Trp His Asp Ala
            35                  40                  45

Val Ser Arg Lys Thr Phe Pro Thr Val Asn Pro Ser Thr Gly Glu Val
        50                  55                  60

Ile Cys Gln Val Ala Glu Gly Asp Lys Glu Asp Val Asp Lys Ala Val
 65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285

Lys Ser Pro Asn Ile Ile Met Ser Asp Ala Asp Met Asp Trp Ala Val
    290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335
```

```
Glu Arg Ser Val Ala Arg Ala Lys Ser Arg Val Val Gly Asn Pro Phe
                340                 345                 350

Asp Ser Lys Thr Glu Gln Gly Pro Gln Val Asp Glu Thr Gln Phe Lys
            355                 360                 365

Lys Ile Leu Gly Tyr Ile Asn Thr Gly Lys Gln Glu Gly Ala Lys Leu
        370                 375                 380

Leu Cys Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
        435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Lys Val Lys Thr Val Thr Val Lys Val
            500                 505                 510

Pro Gln Lys Asn Ser
        515

<210> SEQ ID NO 3
<211> LENGTH: 501
<212> TYPE: PRT
<213> ORGANISM: Homo sapiens

<400> SEQUENCE: 3

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Ser Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190
```

```
Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
                260                 265                 270

Lys Ser Pro Cys Ile Val Leu Ala Asp Ala Asp Leu Asp Asn Ala Val
                275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
                340                 345                 350

Lys Ile Leu Asp Leu Ile Glu Ser Gly Lys Lys Glu Gly Ala Lys Leu
                355                 360                 365

Glu Cys Gly Gly Gly Pro Trp Gly Asn Lys Gly Tyr Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
                420                 425                 430

Phe Thr Lys Asp Ile Asp Lys Ala Ile Thr Ile Ser Ser Ala Leu Gln
                435                 440                 445

Ala Gly Thr Val Trp Val Asn Cys Tyr Gly Val Val Ser Ala Gln Cys
    450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
                500

<210> SEQ ID NO 4
<211> LENGTH: 501
<212> TYPE: PRT
<213> ORGANISM: Homo sapiens

<400> SEQUENCE: 4

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
                20                  25                  30

Val Ser Gly Lys Lys Phe Pro Val Phe Asn Pro Ala Thr Glu Glu Glu
                35                  40                  45

Leu Cys Gln Val Glu Glu Gly Asp Lys Glu Asp Val Asp Lys Ala Val
```

```
            50                  55                  60
Lys Ala Arg Gln Ala Phe Gln Ile Gly Ser Pro Trp Arg Thr Met
 65                  70                  75                  80

Asp Ala Ser Glu Arg Gly Arg Leu Leu Tyr Lys Leu Ala Asp Leu Ile
                     85                  90                  95

Glu Arg Asp Arg Leu Leu Leu Ala Thr Met Glu Ser Met Asn Gly Gly
                    100                 105                 110

Lys Leu Tyr Ser Asn Ala Tyr Leu Asn Asp Leu Ala Gly Cys Ile Lys
                    115                 120                 125

Thr Leu Arg Tyr Cys Ala Gly Trp Ala Asp Lys Ile Gln Gly Arg Thr
                    130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                    165                 170                 175

Ile Trp Lys Ile Gly Pro Ala Leu Ser Cys Gly Asn Thr Val Val Val
                    180                 185                 190

Lys Pro Ala Glu Gln Thr Pro Leu Thr Ala Leu His Val Ala Ser Leu
                    195                 200                 205

Ile Lys Glu Ala Gly Phe Pro Pro Gly Val Val Asn Ile Val Pro Gly
210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                    245                 250                 255

Ala Ala Gly Lys Ser Asn Leu Lys Arg Val Thr Leu Glu Leu Gly Gly
                    260                 265                 270

Lys Ser Pro Cys Ile Val Leu Ala Asp Ala Asp Leu Asp Asn Ala Val
                    275                 280                 285

Glu Phe Ala His His Gly Val Phe Tyr His Gln Gly Gln Cys Cys Ile
                    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                    325                 330                 335

Thr Pro Gly Val Thr Gln Gly Pro Gln Ile Asp Lys Glu Gln Tyr Asp
                    340                 345                 350

Lys Ile Leu Asp Leu Ile Glu Ser Gly Lys Lys Glu Gly Ala Lys Leu
                    355                 360                 365

Glu Cys Gly Gly Gly Pro Trp Gly Asn Lys Gly Tyr Phe Val Gln Pro
                    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                    405                 410                 415

Val Ile Lys Arg Ala Asn Asn Thr Phe Tyr Gly Leu Ser Ala Gly Val
```

-continued

```
                420                 425                 430
Phe Thr Lys Asp Ile Asp Lys Ala Ile Thr Ile Ser Ser Ala Leu Gln
            435                 440                 445
Ala Gly Thr Val Trp Val Asn Cys Tyr Gly Val Val Ser Ala Gln Cys
        450                 455                 460
Pro Phe Gly Gly Phe Lys Met Ser Gly Asn Gly Arg Glu Leu Gly Glu
465                 470                 475                 480
Tyr Gly Phe His Glu Tyr Thr Glu Val Lys Thr Val Thr Val Lys Ile
            485                 490                 495
Ser Gln Lys Asn Ser
            500

<210> SEQ ID NO 5
<211> LENGTH: 453
<212> TYPE: PRT
<213> ORGANISM: Homo sapiens

<400> SEQUENCE: 5

Met Ser Lys Ile Ser Glu Ala Val Lys Arg Ala Pro Ala Ala Phe Ser
1               5                   10                  15
Ser Gly Arg Thr Arg Pro Leu Gln Phe Arg Ile Gln Gln Leu Glu Ala
            20                  25                  30
Leu Gln Arg Leu Ile Gln Glu Gln Gln Glu Leu Val Gly Ala Leu
        35                  40                  45
Ala Ala Asp Leu His Lys Asn Glu Trp Asn Ala Tyr Tyr Glu Glu Val
    50                  55                  60
Val Tyr Val Leu Glu Glu Ile Glu Tyr Met Ile Gln Lys Leu Pro Glu
65                  70                  75                  80
Trp Ala Ala Asp Glu Pro Val Lys Thr Pro Gln Thr Gln Gln Asp
            85                  90                  95
Glu Leu Tyr Ile His Ser Glu Pro Leu Gly Val Val Leu Val Ile Gly
            100                 105                 110
Thr Trp Asn Tyr Pro Phe Asn Leu Thr Ile Gln Pro Met Val Gly Ala
        115                 120                 125
Ile Ala Ala Gly Asn Ser Val Val Leu Lys Pro Ser Glu Leu Ser Glu
    130                 135                 140
Asn Met Ala Ser Leu Leu Ala Thr Ile Ile Pro Gln Tyr Leu Asp Lys
145                 150                 155                 160
Asp Leu Tyr Pro Val Ile Asn Gly Gly Val Pro Glu Thr Thr Glu Leu
                165                 170                 175
Leu Lys Glu Arg Phe Asp His Ile Leu Tyr Thr Gly Ser Thr Gly Val
            180                 185                 190
Gly Lys Ile Ile Met Thr Ala Ala Lys His Leu Thr Pro Val Thr
        195                 200                 205
Leu Glu Leu Gly Gly Lys Ser Pro Cys Tyr Val Asp Lys Asn Cys Asp
    210                 215                 220
Leu Asp Val Ala Cys Arg Arg Ile Ala Trp Gly Lys Phe Met Asn Ser
225                 230                 235                 240
Gly Gln Thr Cys Val Ala Pro Asp Tyr Ile Leu Cys Asp Pro Ser Ile
                245                 250                 255
Gln Asn Gln Ile Val Glu Lys Leu Lys Lys Ser Leu Lys Glu Phe Tyr
            260                 265                 270
Gly Glu Asp Ala Lys Lys Ser Arg Asp Tyr Gly Arg Ile Ile Ser Ala
        275                 280                 285
```

```
Arg His Phe Gln Arg Val Met Gly Leu Ile Glu Gly Gln Lys Val Ala
    290             295                 300

Tyr Gly Gly Thr Gly Asp Ala Ala Thr Arg Tyr Ile Ala Pro Thr Ile
305             310              315                 320

Leu Thr Asp Val Asp Pro Gln Ser Pro Val Met Gln Glu Glu Ile Phe
                325             330                 335

Gly Pro Val Leu Pro Ile Val Cys Val Arg Ser Leu Glu Glu Ala Ile
                340             345                 350

Gln Phe Ile Asn Gln Arg Glu Lys Pro Leu Ala Leu Tyr Met Phe Ser
        355             360                 365

Ser Asn Asp Lys Val Ile Lys Lys Met Ile Ala Glu Thr Ser Ser Gly
    370             375                 380

Gly Val Ala Ala Asn Asp Val Ile Val His Ile Thr Leu His Ser Leu
385             390             395                 400

Pro Phe Gly Gly Val Gly Asn Ser Gly Met Gly Ser Tyr His Gly Lys
                405             410                 415

Lys Ser Phe Glu Thr Phe Ser His Arg Arg Ser Cys Leu Val Arg Pro
            420             425                 430

Leu Met Asn Asp Glu Gly Leu Lys Val Arg Tyr Pro Pro Ser Pro Ala
        435             440                 445

Lys Met Thr Gln His
    450
```